US008470805B2

(12) United States Patent
Chen

(10) Patent No.: US 8,470,805 B2
(45) Date of Patent: Jun. 25, 2013

(54) PROCESSES FOR PREPARING PIPERAZINIUM SALTS OF KMUP AND USE THEREOF

(75) Inventor: Ing-Jun Chen, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 193 days.

(21) Appl. No.: 12/878,451

(22) Filed: Sep. 9, 2010

(65) Prior Publication Data
US 2011/0136767 A1   Jun. 9, 2011

Related U.S. Application Data

(63) Continuation of application No. 12/630,368, filed on Dec. 3, 2009.

(30) Foreign Application Priority Data

Jan. 29, 2010  (TW) .............................. 99102735 A

(51) Int. Cl.
*A61K 31/60* (2006.01)
*A61K 31/497* (2006.01)
*C07D 473/00* (2006.01)

(52) U.S. Cl.
USPC ....... 514/161; 514/252.16; 514/249; 544/270

(58) Field of Classification Search
USPC ..................... 544/270; 514/161, 252.16, 249
See application file for complete search history.

(56) References Cited

U.S. PATENT DOCUMENTS

| | | | | |
|---|---|---|---|---|
| 2,748,127 | A * | 5/1956 | Baltzly et al. ................. | 544/396 |
| 3,703,519 | A * | 11/1972 | Henderson ..................... | 544/403 |
| 4,198,507 | A | 4/1980 | Barry et al. | |
| 4,231,938 | A | 11/1980 | Monaghan et al. | |
| 4,346,227 | A | 8/1982 | Terahara et al. | |
| 4,426,383 | A * | 1/1984 | Sugimoto et al. ........ | 514/252.16 |
| 4,444,784 | A | 4/1984 | Hoffman et al. | |
| 4,739,073 | A | 4/1988 | Kathawala | |
| 5,006,530 | A | 4/1991 | Angerbauer et al. | |
| 5,159,104 | A | 10/1992 | Dabora et al. | |
| 5,177,080 | A | 1/1993 | Angerbauer et al. | |
| 5,260,440 | A | 11/1993 | Hirai et al. | |
| 5,298,627 | A | 3/1994 | Butler et al. | |
| 6,002,021 | A | 12/1999 | Yang et al. | |
| 6,100,407 | A | 8/2000 | Van Dalen et al. | |
| 6,294,680 | B1 | 9/2001 | Vries et al. | |
| 6,316,460 | B1 | 11/2001 | Creekmore et al. | |
| 6,979,687 | B1 | 12/2005 | Chen | |
| 7,390,504 | B2 | 6/2008 | Tunac | |
| 7,550,468 | B2 | 6/2009 | Chen | |
| 2005/0209243 | A1* | 9/2005 | Chen ....................... | 514/252.16 |
| 2008/0312249 | A1 | 12/2008 | Chen | |

FOREIGN PATENT DOCUMENTS

TW   200848044   1/2006
WO      9513283   5/1995

OTHER PUBLICATIONS

Arayne et al. Med Chem Res. (2010) 19:717-731.*
Chung et al., "The xanthine derivative KMUP-1 inhibits models of pulmonary artery hypertension via increased NO and cGMP-dependent inhibition of RhoA/Rho kinase," British Journal of Pharmacology, (Jun. 2010) 160(4):971-986.
Evans et al., Effects of HMG-CoA Reductase Inhibitors on Skeletal Muscle: Are all Statins the Same?, Drug Safety (2002) 25(9):649-663.
Hiro et al., Effects of Intensive Statin Therapy of Regression of coronary Atherosclerosis in Patients with Acute Coronary Syndrome: A Multicenter Randomized Trial Evaluated by Volumetric Intravascular Ultrasound Using Pitavastatin Versus Atorvastatin (Japan-ACS[Japan Assessment of Pitavastatin and Atorvastatin in Acute Coronary Syndrome] Study), J. Am. Coll. Cardiol. (2009) 54:293-302.
Jacobson TA, "Myopathy with statin-fibrate combination therapy: clinical considerations," Nat. Rev. endocrinol. (Sep. 2009) 5(9);507-518.
Lin et al., "KMUP-1 relaxes rabbit corpus cavernosum smooth muscle in vitro and in vivo: involvement of cyclic GMP and $K^+$ channels," British Journal of Pharmacology (2002) 135:1159-1166.
Lipid Research Clinics Program, "The Lipid Research Clinics Coronary Primary Prevention Trial Results: Reduction in Incidence of Coronary Heart Disease," JAMA (1984) 251(3):351-374.
Liu et al., "cGMP-Enhancing- and $\alpha_{1A/\alpha1D}$—Andrenoceptor Blockade-Derived Inhibition of Rho-Kinase by KMUP-1 Provides Optimal Prostate Relaxation and Epithelial Cell Anti-Proliferation Efficacy," The Prostate (2007) 67:1397-1410.
Versmissen et al., "Efficacy of statins in familial hypercholesterolaemia: a long term cohort study," BMJ (Jan. 21, 2009) 338:a3041.
Wu et al., "A xanthine-based KMUP-1 with cyclic GMP enhancing and $K^+$ channels opening activities in rat aortic smooth muscle," British Journal of Pharmacology (2001) 134:265-274.

(Continued)

*Primary Examiner* — Shirley V Gembeh
(74) *Attorney, Agent, or Firm* — Volpe and Koenig, P.C.

(57) ABSTRACT

A series of monoquarternary piperazium salts including a structure of a formula I or II are provided. In formula I or II, $R_1$, $R_a$, and RX are as defined in the specification. The monoquarternary piperazium salt of KMUP or piperazine disclosed in the present invention is characterized by being presented in a pro-drug form and having various pharmaceutical functions.

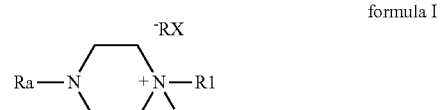

formula I

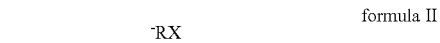

formula II

12 Claims, 5 Drawing Sheets

OTHER PUBLICATIONS

Wu et al., "KMUP-1, a xanthine derivative, induces relaxation of guinea-pig isolated trachea: the role of the epithelium, cyclic nucleotides and $K^+$ channels," British Journal of Pharmacology (2004) 142:1105-1114.

Wu et al., "Inhibition of Proinflammatory Tumor Necrosis Factor-α-Induced Inducible Nitric-Oxide Synthase by Xanthaine-based 7-[2-[4-(2-Chlorobenzene)piperazinyl]ethyl]-1,3-dimethylxanthine (KUMP-1) and 7-[2-[4-(4-Nitrobenzene)piperazinyl]ethyl]-1,3-dimethylxanthine (KUMP-3) in Rat Trachea: The involvement of Soluble Guanylate Cyclase and Protein Kinase G," Mol Pharmacol (2006) 70:977-985.

Wu et al., "KMUP-1 activates $BK_{Ca}$ channels in basilar artery myocytes via cyclic nucleotide-dependent protein kinases," British Journal of Pharmacology (2005) 146:862-871.

Van Straten et al., "Analysis of Organic Acids in Aqueous Samples," Agilent Technologies (2004).

Taiwanese Office Action, Taiwanese Application No. 099102735, filed Jan. 29, 2010.

* cited by examiner (a) KMUP-1 HCl (1)

(b) KMUP-1-Citric acid (2)

(c) manufacturing KMUP-1-statin complex compound

-Atorvastatinic acid(10)

non-steroid anti-inflammatory (NSAIDs) carboxylic acids

-Methotrexate(11) | -Indomethacin(12)

anti-diabetic carboxylic acids

-Repaglinide (13) | -Nateglinide(14)

| anti-asthmatic carboxylic acids | |
|---|---|
|  |  |
| -Cromolyn (15) | - Montelukast (16) |
| lipid lowering of fibric acid derivative | |
|  |  |
| - Gemfibrozil (17) | -Fibric acid (18) |
|  | |
| -γ-polyglutamic acid (22) | |

Di-Simvastatinic acid piperazinium salt (19)

Di-Rosuvastatinic acid piperazinium salt (20)

Di-Atorvastatinic acid piperazinium salt (21)

|  |  |
|---|---|
| KMUP-3 HCl (22) | KMUP-2 HCl (23) |

US 8,470,805 B2

PROCESSES FOR PREPARING PIPERAZINIUM SALTS OF KMUP AND USE THEREOF

FIELD OF THE INVENTION

The present invention relates to the complex compounds and their preparation thereof used as the pro-drugs of different pharmaceutical functions. Particularly, the present invention first relates to the preparation of quarternary piperazium salts of KMUP compounds and the anti-hypercholesterolemia activity of KMUP-1 as well as pleitropic effects of KMUP-associated piperazinium salts.

BACKGROUND OF THE INVENTION

Statins, which have a general structure of

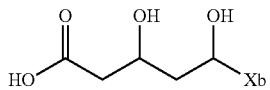

wherein Xb represents the remained structure part of the open-lactone statins, are currently the therapeutically effective drugs available for reducing the concentration of the low-density lipoprotein (LDL) particle having the risk of cardiovascular disease existing in the bloodstream of patients. A high concentration of LDL in the bloodstream has been linked to the formation of coronary lesions and would obstruct the blood flow and cause thrombosis. To date, statins have been used in the treatments of hypercholesterolemia (Versmissen J, et al., Efficacy of statins in familial hypercholesterolaemia: a long term cohort study. BMJ. 2009 Jan 21; 338:a3041), hyper-lipoproteinemia, atherosclerosis (Hiro, T., et al., Effect of Intensive Statin Therapy on Regression of Coronary Atherosclerosis in Patients With Acute Coronary Syndrome. J Am Coll Cardiol, 2009; 54:293-302), benigh prostate hyperplasia (BPH) and osteoporosis by decreasing osteoclast formation. In contrast, KMUP-1 is the first exposed as a new non-statin 3-hydroxy-3-methylglutaryl-co-enzyme A (HMG-CoA) inhibitor in this invention, compared to previous invention described in patent U.S. Pat. No. 7,550,468 B2 (2009).

U.S. Pat. No.7,390,504 discloses a water soluble salt formula consisting of a dihydroxy and open-lactone statins and a fibric acid. However, Evans M. et al. have found that statins incur the untoward effects of myotoxicity and rhabdomyolysis, especially utilized in combination with the fibric acid drugs (Drug Safety, Volume 25, Number 9, 2002, pp. 649-663(15)). The recent study of Jacobson T A can't overcome the above-mentioned risk as well although it is considered that there has been none of the data obtained from a large-scale experiment for supporting the risk resulted from combing the statins and the fibric acid drugs (Nat Rev Endocrinol. 2009).

SUMMARY OF THE INVENTION

A complex compound represented by the following formula

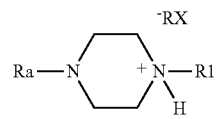

or formula

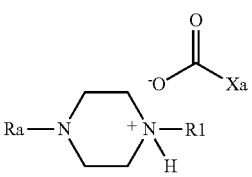

is provided, wherein $R_1$ may be a hydrogen, or a benzene ring having a substituting group being a halogen atom, an amino group, a nitro group, a C1~C5 alkyl group or a C1~C5 alkoxy group; $R_a$ is one of a hydrogen and a xanthine group substituted with a substituting group being selected from a group consisting of a halogen atom, an amino group, a nitro group, a C1~C5 alkyl group and a C1~C5 alkoxy group; RX contains a carboxylic group which donated from a group consisting of a mineral acid, an organic acid, a statin, a fibric acid derivative, a member of non-steroid anti-inflammatory drugs (NSAIDs), an anti-diabetic drug and an anti-asthmatic drug; $RX^-$ may be an anion of the above-mentioned groups carrying a negative charge.

The above-mentioned halogen refers to fluorine, chlorine, bromine and iodine.

According to the present invention, a compound of formula (I) where $R_1$ and $R_a$ are hydrogen refers to a piperazine salt. Nevertheless, formula (I) may represent as formula

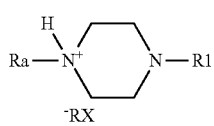

or formula

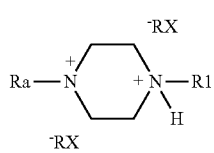

with carboxylic dimers according to the amount of the reacting acid and stereo combination. When a partial structure except the carboxyl group in the organic acid, the statins, the fibric acid derivative, the NSAIDs, the anti-diabetic drug and the anti-asthmatic drug are represented as Xa, formula (I) may show as formula (II) (i.e. formula (IA) may show as formula

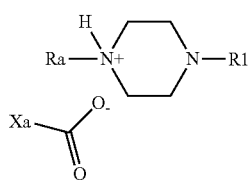

and formula (IB) may show as formula

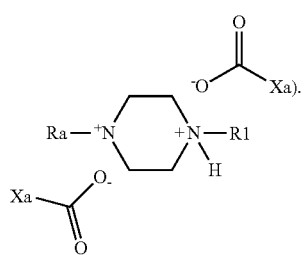

According to the present invention, a compound of formula (I) or formula (II), where $R_1$ and $R_a$ are not hydrogen, referred to as KMUP complex salts. In which, a chlorobenzene-derived 7-[2-[4-(2-chlorobenzene) piperazinyl]ethyl]-1,3-dimethylxanthine is referred to as KMUP-1 hereafter. KMUP-1 is a xanthine-based KMUP derivative that is obtained by reacting 7-ethylchloro-theophylline with 1-(2-chlorophenyl) piperazine). KMUP-1 has been proved to cause the potassium ion channels opening and the relaxation of the aorta (Wu et al., 2001), corporeal carvenosa and tracheal smooth muscle (Wu et al., 2004) by activating soluble guanylyl cyclase (sGC), inhibiting phosphodiesterase (PDE) and increasing cellular cyclic adenosine monophosphate (cAMP), 3',5'-cyclic guanosine monophosphate and protein kinase G (PKG).

KMUP-1 can also inhibit the phenylepherine-induced contraction by inhibiting $\alpha_{1A}/\alpha_{1D}$-adenoreceptors, increases cAMP/cGMP amounts and inhibits the phenylepherine-induced Rho kinase 2 (ROCK2) expressions in prostatic smooth muscles. Furthermore, KMUP-1 may serve as an inhibitor of phosphodiesterase-5A (PDE5A)/ROCK2 for suppressing the growth of normal human prostatic cell line (PZ-HPV-7) to arrest the cell cycle staying at $G_0/G_1$ phase and increase p21 protein expressions (Liu et al., 2007).

Besides, KMUP-1 has also been proved to increases the $Ca^{2+}$-activated potassium ($Bk_{ca}$) currents by enhancing the cGMP-dependent protein kinase activity, and such activation will cause physiologically voltage-dependent calcium channel closing and cerebral artery relaxation (Wu et al., 2005). Accordingly, KMUP-1 has an advantage in treating hypertension. KMUP-1 may inhibit the expressions of the inducible nitric-oxide synthase (iNOS) and the tumor necrosis factor-$\alpha$ (TNF-$\alpha$) in rat tracheal smooth muscle cells (TSMCs), which is involved in the sGC/cGMP/PKG pathway but not in the cyclooxygenase-2 (COX-2) expression pathway (Wu et al., 2006).

As shown in the present disclosures, KMUP-1 has some pleiotropic activities such as lipid lowering and inhibition activity of Rho-kinase expression. KMUP-1 possesses endothelium nitric oxide synthase (eNOS) activation and displays the statin-like activities in inhibiting pulmonary artery hypertension and enhancing cGMP (Wu et al., 2006; Chung et al., 2010). Therefore, KMUP-1, KMUP-2 and KMUP-3 disclosed in the above-mentioned U.S. Pat. Nos. 6,979,687 and 7,550,468 are classified as KMUP compounds. These KMUP compounds, belong to the 1,4-disubstituted piperazine derivatives family, can be used for the preparation of KMUP- or piperazine-based quaternary piperazinium salts in the present invention.

In order to overcome some undesired effect existing in the commercial statin drugs and broaden the active spectrum of lipid-lowering cells in various organs or tissues, an ionic complex formation between KMUP-1 and statin is formed in the present invention that has the potential advantages in the treatments of hypercholesterolemia, hyper-lipoproteinemia, atherosclerosis, pulmonary arterial hypertension, diabetes, ischemia disease, BPH, neuro-inflammation and influenza. It is proved that the piperazinium salts of KMUP-1 and the statins, generally referred as "KMUP-1-Statin complex salt" may demonstrate pro-drug and multiple therapeutic functions so as to lower the risk of the above side effects. Accordingly, the present invention also provides mineral acid salt and organic acid salts formed by KMUP-1 or piperazine (e.g. the KMUP-1 hydrochloric acid salt (1) in FIG. 1(a) or KMUP-1 citric acid salt (2) in FIG. 1(b)), which become a pharmaceutical composition by adding statins and excipients. The pharmaceutical composition shows the prodrug and the multiple therapeutic functions so as to lower the risk of the untoward side effects of statins, while the KMUP-1 salts of the statins are administered to reduce the untoward side effects but to specifically potentiate the lipid-lowering activity of statins. Ionic complex such as KMUP-1-Statinic acid of KMUP-1 and statin is suggested to reduce the dosage of the statins and KMUP-1 itself in the clinics.

According to the present invention, a sufficient amount of piperazium group of KMUP or piperazine may react with statin derivatives containing a carboxyl group to form a monoquaternary piperazium salt. Further, the term "RX" group can be referred to the statins containing a derivative of the carboxyl group and can react with the piperazine group of KMUP or their piperazine moiety to prepare the above KMUP or piperazine monoquaternary piperazium salt according to the method in the present invention. The synthesized monoquaternary piperazium salts may show a pro-drug and multiple therapeutic functions in the body via a chemical or an enzymatic hydrolysis.

According to the present invention, KMUP-1 and statins are matched by figures and a table to illustrate embodiments for preparing the KMUP- or piperazine-based monoquaternary piperazium salts of the present invention. Thereby, KMUP-1 may represent KMUP (KMUP-1, KMUP-2 or KMUP-3) or the involved piperazine moiety, and the statins may represent the above-mentioned "RX" or "RX−" compounds involved in preparing the monoquaternary piperazium salts in the present invention, if necessary.

According to the present invention, the statins, the fibric acid derivatives for lowering blood lipid, the NSAIDs, the anti-asthmatic drug, the anti-diabetic drug and the prostacyclin, which all chemically having a carboxyl moiety, can ionically combine with piperazine moiety of another drug via a chemical pretreatment. Thus, the lactone ring, ester and protected derivatives of the statins are available to prepare the above KMUP- and piperazine-based monoquaternary piperazium salts in the present invention.

The term "RX" in the present invention may be a mineral acid or an organic acid, selecting from the organic acids including citric acid, fumaric acid, maleic acid, nicotinic acid, isonicotinic acid, tartaric acid, succinic acid, adipic acid, fatty acid, methanesulfonic acid and phenoxylevulinic acid, or the mineral acids including hydrochloric acid (HCl), hydrobromic acid (HBr), hydroiodic acid (HI), sulfuric acid ($H_2SO_4$), nitric acid ($HNO_3$), phosphoric acid ($H_3PO_4$), sodium dihydrogen posphate ($NaH_2PO_4$) and disodium hydrogen phosphate ($Na_2HPO_4$). The acids react with KMUP or piperazine to form a monoquaternary piperazium salt. These salt type prodrugs are able to show the therapeutic functions of KMUP in the body via a chemical or an enzyme hydrolysis.

As shown in FIG. 1(c), the preparation for KMUP-1 monoquaternary piperazium salt disclosed in the present invention is to connect the 2-chlorobenzene group (R1) and the ethyl-1,3-dimethyl-xanthine group (Ra) shown by the structure of the piperazium group of KMUP-1, and to connect the remained moiety (R1) of the statins through the bridging by negative carboxylate ion. Specifically, KMUP-1 is dissolved in a mixture of a C1-C4 alcohol (i.e. the methanol and the ethanol) and a mineral acid (i.e HCl) to react under 40° C.-70° C. or cooled under 4° C. to prevent the cleavage of their hydrolyzable group such as ester or amide derivatives. An alcohol is added into the above solution for crystallization and a KMUP-1 salt is obtained by filtration. Additionally, a statin is dissolved in an alcohol solution and poured into a flask with a magnetic stir. The sodium, potassium or calcium hydroxide or the ammonium hydroxide solution and the filtrate resulting from the alcohol reaction of the KMUP-1 salt are added into the flask and then are continuously stirred with increasing temperature. After quickly filtrating and crystallizing in the filtrate, the KMUP-1 monoquaternary piperazium salt is obtained. The therapeutic functions of KMUP-1 and statin will be revealed in the body via a chemical or an enzymatic hydrolysis. Therefore, KMUP-1-Statinic acids complex salt belongs to a pro-drug of KMUP-1 and each statin, having multiple therapeutic functions described in this invention.

Since KMUP-1 has cGMP enhancing activity (Wu et al., 2006) and increases anti-platelets aggregation activity for the anti-inflammation drug. The KMUP-1 monoquaternary complex formed by the NSAIDs containing a carboxyl group shows the pro-drug and therapeutic functions in the body via a chemical or an enzymatic hydrolysis. Furthermore, KMUP-1 can combine with the carboxyl moiety of the fibric acid to replace the mixing benefits of statin and fibric acid displaying different combination for reducing the muscle toxicity of statins. The monoquaternary complex formed by the methotrexate with a di-carboxyl structure and KMUP-1 can be use for rheumatoid arthritis and chemical therapy for anti-cancer. The monoquaternary complex formed by the carboxyl structure of the prostacyclin ($PGI_2$) and KMUP-1 can be used in treating pulmonary hypertension, potentially with merits of $PGI_2$ and KMUP-1.

Both of KMUP-1 and statin have pleitropic effects except lipid-lowering activity. The combination of KMUP and various active agents through bridging them by a specific carboxyl anion may provide the enhanced lipid-lowering, anti-inflammatory, anti-asthmatic and anti-diabetic activity, the so-called statin-like pleitropic effects of KMUP-1.

In the cholesterol biosynthesis pathway, statins inhibit the production of the cholesterol by inhibiting the activity of HMG-CoA. The conversion from HMG into mevalonate catalyzed by HMG-CoA reductase is a rate-limit step in the cholesterol biosynthesis. Reduced cholesterol amount increases the numbers of low-density lipoprotein (LDL) receptors and reduces the concentration of the corresponding LDL granule in the blood. Thereby, previous clinical studies have indicated that reduced LDL amount in the blood can reduce the risk of the coronary heart disease (Lipid Research Clinics Program. 1984).

Currently available statins widely include atorvastatin, cerivastatin, fluvastatin, lovastatin, mevastatin, pravastatin, rosuvastatin and simvastatin. The chemical structures of various statins are presented as Formula (III) and their chemical names are listed in Table 1. Lovastatin (disclosed in U.S. Pat. No. 4,231,938) and simvastatin (disclosed in U.S. Pat. No. 4,444,784) are administered in a lactone form. After being absorbed, the lactone ring is opened in the liver by a chemical or an enzymatic hydrolysis, and the active hydroxy acid (statinic acid) is generated. Pravastatin (disclosed in U.S. Pat. No. 4,346,227) is administered as the sodium salt. Fluvastatin (disclosed in U.S. Pat. No. 4,739,073) and cerivastatin (disclosed in U.S. Pat. Nos. 5,006,530 and 5,177,080), also administered as the sodium salts, are entirely synthetic compounds that are structurally distinct from a kind of drug to which the fungal derivatives including a hexahydronaphthalene ring belong. Atorvastatin and two "superstatins" novel lipid-lowering drugs, rosuvastatin and pitavastatin, are administered as calcium salts.

TABLE 1

Chemical names of the Statins

| Commercial products | Chemical names |
|---|---|
| Atorvastatin intermediate L-1 | tert-Butyl(4R,6R)-2-[[[6-(2-4-fluorophenyl)-5-isopropyl-3-phenyl-4-(phenylcarbamoyl)pyrrol-1-yl]ethyl]-2,2-dimethyl-1,3-dioxan-4-yl]acetate (4R,6R)-6-[2-[2-(4-fluorophenyl)-5-(1-methylethyl)-3-phenyl-4-[(phenylamino)carbonyl]-1H-pyrrol-1-yl]ethyl]-2,2-dimethyl-1,3-Dioxane-4-acetic acid 1,1-dimethylethyl ester |
| Atorvastatin Calcium salt | [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt |
| Atorvastatin lactone | 2R-trans)-5-(4-fluorophenyl)-2-(1-methylethyl)-N,4-diphenyl-1-[2-tetrahydro-4-hydroxy-6-oxo-2H-pyran-2-yl)ethyl]-1H-pyrrole-3-carboxamide |
| Cerivastatin sodium salt | sodium (E,3R,5S)-7-[4-(4-fluorophenyl)-5-(methoxymethyl)-2,6-di(propan-2-yl)pyridin-3-yl]-3,5-dihydroxyhept-6-enoate |
| Fluvastatin sodium salt | sodium (E,3S,5R)-7-[3-(4-fluorophenyl)-1-propan-2-ylindol-2-yl]-3,5-dihydroxyhept-6-enoate |
| Lovastatin sodium salt | 1S-[1a(bS,dS),2a,6b,8b(R),8aa]]-1,2,6,7,8,8a-Hexahydro-b,d-dihydroxy-2,6-dimethyl-8-(2-methyl-1-oxobutoxy)-1-naphthaleneheptanoic acid monosodium salt |
| Mevastatin ester | 2-Methyl-butanoic acid [1S-[1-α(R*),7-β,8-β(2S*,4S*),a-β]]-1,2,3,7,8,8a-hexahydro-7-methyl-8-[2-(tetrahydro-4-hydroxy-6-oxo-2H-pyran-2-yl)ethyl]-1-naphthalenyl ester |
| Pitavastatin calcium salt | (3R,5S,6E)-7-[2-cyclopropyl-4-(4-fluorophenyl)-3-quinolyl]-3,5-dihydroxy-6-heptenoate |
| pravastatin sodium salt | [1S-[1a(bS,dS),2a,6b,8b(R),8aa]]-1,2,6,7,8,8a-Hexahydro-b,d,6-trihydroxy-2-methyl-8-(2-methyl-1-oxobutoxy)-1-naphthalene-heptanoic acid monosodium salt |
| Rosuvastatin Calcium salt | bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium |
| Simvastatin Sodium salt | Ammonium (3R,5R)-7-[(1S,2S,6R,8S,8aR)-8-(2,2-dimethylbutyryloxy)-1,2,6,7,8,8a-hexahydro-2,6-dimethyl-1-naphthyl]-3,5-dihydroxyheptanoate |

Atorvastatin is disclosed in U.S. Pat. No. 4,681,893, and the character that the free acid of atorvastatin is prone to lactonization has been disclosed in U.S. Pat. No. 5,273,995. Atorvastatin calcium salt can be reacted with KMUP-1 HCl, to perform the double decomposition exchange reaction and to release calcium chloride in a solvent system of water and ethyl alcohol mixture. Such statin calcium salt contacts with the KMUP-1 HCl to form a water soluble calcium chloride. The non-salt type free acid statin will react with the piperazium group of KMUP-1 and form the "KMUP-1-statins complex salt" or more favorable "KMUP-1-Statinic acid complex salt".

U.S. Pat. No. 5,298,627 discloses that (4R-cis)-1-[2-[6-[2-(diphenylamino)-2-oxoethyl]-2,2-dimethyl-1,3-dioxan-4-yl]ethyl]-5-(4-fluorophenyl)-2-(1-methylethyl)-N,4-diphenyl-1H-pyrrole-3-carboxamide is dissolved in methanol and reacted with hydrochloric acid to form [R-(R*,R*)]-5-(4-fluorophenyl)-β,δ-dihydroxy-2-(1-methylethyl)-N,N,4-triphenyl-3-[(phenylamino)carbonyl]-1H-pyrrole-1-heptanamide, which is mixed with methanol and sodium hydroxide. The filtrate is washed with tert-butyl methyl ester and the aqueous layer is acidified by using hydrochloric acid and extracted with tert-butyl methyl ester to afford the sodium salt of [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid. The sodium salt is converted to the Statinic acid complex salt of the KMUP monoquarternary piperazium group (KMUP-1-Statinic acid) by adding equal molar KMUP HCl.

An analogous acetamide structure in atorvastatin can be converted into a KMUP monoquarternary piperazium complex salt. For example, (4R-cis)-6-(2-aminoethyl)-2,2-dimethyl-N,N-bis(phenylmethyl)-1,3-dioxane-4-acetamide is firstly converted to [R-(R*,R*)]-5-(4-fluorophenyl)-β,δ-dihydroxy-2-(1-methylethyl)-4-phenyl-3-[(phenylamino)carbonyl]-N,N-bis(phenylmethyl)-1H-pyrrole-1-heptanamide which is reacted and further converted to the Statinic acid complex salt with KMUP monoquarternary piperazium group. Moreover, (4R-cis)-6-
(2-aminoethyl)-N,N-diethyl-2,2-dimethyl-1,3-dioxane-4-acetamide is converted to [R-(R*,R*)]-N,N-diethyl-5-(4-fluorophenyl)-
β,δ-dihydroxy-2-(1-methylethyl)-4-phenyl-3-[(phenylamino)carbonyl]-1H-pyrrole-1-heptanamide which is further converted to a complex salt of the KMUP-Statinic acid. Under an analogous reaction, (4R-cis)-6-(2-aminoethyl)-N-butyl-N,2,2-trimethyl-1,3-dioxane-4-acetamide is converted to [R-(R*,R*)]-N-butyl-5-(4-fluorophenyl)-
β,δ-dihydroxy-N-methyl-2-(1-methylethyl)-4-phenyl-3-[(phenylamino)carbonyl]-1H-pyrrole-1-heptanamide which is reacted to form a complex salt of the KMUP-Statinic acid. The (4R-cis)-6-(2-aminoethyl)-N-(1,1-dimethylethyl)-
2,2-dimethyl-N-(phenylmethyl)-1,3-dioxane-4-acetamide is converted to [R-(R*,R*)]-N-(1,1-dimethylethyl)-5-(4-fluorophenyl)-β,δ-dihydroxy-2-(1-methylethyl)-4-phenyl-3-[(phenylamino)carbonyl]-N-(phenylmethyl)-1H-pyrrole-1-heptanamide which is further reacted to form a complex salt of the KMUP-Statinic acid. Furthermore, the (4R-cis)-1-[[6-(2-aminoethyl)-2,2-dimethyl-1,3-dioxan-4-yl]-acetyl]piperidine is also converted to [R-(R*,R*)]-1-[3,5-dihydroxy-7-oxo-7-(1-piperidinyl)heptyl]-5-(4-fluorophenyl-2-(1-methylethyl)-N-4-diphenyl-1H-pyrrole-3-carboxamide which further forms a complex salt of the KMUP-1-Statinic acid with the KMUP-1 monoquarternary piperazium group.

The commercial statin calcium salt is a combination of two molecules of statins and one molecule of calcium. The so-called hemicalcium salt is referred to a combination of one molecule of statins and one molecule of calcium. Rosuvastatin, its calcium salt and its lactone form are disclosed in U.S. Pat. No. 5,260,440, which obtains the methyl ester of rosuvastatin under reflux followed by reduction with $NaBH_4$. Further, the ester is then hydrolyzed with sodium hydroxide in ethanol solution at room temperature, followed by removal of the ethanol and addition of ether, to obtain the sodium salt of rosuvastatin. Additionally, the rosuvastatin composition disclosed in U.S. Pat. No. 6,316,460 includes a multivalent phosphate salt of rosuvastatin. According to the process of the present invention, the rosuvastatin sodium salt is dissolved in water under a nitrogen atmosphere, and the KMUP is then added into the solution. After adding the KMUP followed by the precipitation and crystallization, the KMUP-Rosuvastatinic acid complex salt, a monoquarternary piperazium salt, is formed.

Statins can be prepared through an intermediate in which one or both of the hydroxyls in the pentanoic acid diol group (open-ring form) or the hydroxyl of the lactone (ring-closed form) are protected via a hydrolyzable protecting group and the carboxyl group is protected via an ester derivative. U.S. Pat. No. 5,260,440 discloses the preparation of rosuvastatin. U.S. Pat. Nos. 6,002,021 and 4,444,784 disclose a process for preparing simvastatin, which use the cyclic protecting group such as the dioxane, the cyclic sulfate, the cyclic phosphate and the borylidene to substitute the alkyl or aryl timely. Additionally, WO 95/13283 discloses the boric acid as the protecting group, the U.S. Pat. No. 5,159,104 discloses an esterification proceeded by the acetic anhybride and U.S. Pat. No. 6,100,407 also discloses some protecting groups.

Piperazium group of KMUP reacts with the carboxylic acid moiety of statins in the present invention. The atorvastatin can be converted into atorvastatin semicalcium salt although it is protected by the ester group. The process for preparing KMUP monoquarternary piperazium group-statin salt described in the present invention is also applicable in preparing the ester derivative and the protected derivative of statin. In the process, the metallic hydroxide such as sodium, potassium and calcium and the ammonia hydroxide are added to mildly heat the reaction of a mixture solution of the ester derivative of the statin, KMUP, water and $C_1$ to $C_4$ alcohol for preventing the decomposition of the statin and the prodrug thereof.

Preferred statins are atorvastatin, lovastatin, pitavastatin, rosuvastatin and simvastatin, the statin structure of those drugs are hydrolized by metallic hydroxide, such as sodium, potassium, calcium, and ammonia hydroxide, and acids useful to hydrolyze the ester group of statin.

The formation of KMUP-1-Statinic acid complex from KMUP-1 HCl salt is easily obtained by reacting KMUP-1 HCl with the equal molar sodium hydroxide in the presence of hydrolyzable statins or statins ester and derivatives. The sodium ion precedes the equal molar neutralization activity with the HCl part of KMUP-1 HCl salt, and the resulted NaCl is dissolved in the hydrated alcohol solution. The statin shows the ionic state or the free state in a mixing solution of $C_1$-$C_4$ lower alcohol (i.e. the ethanol and the isopropanol) and water, or being mixed with other unreacted ester derivative of the statin. By following the amount of each statin derivative hydrolyzed by the sodium hydroxide, the term "sufficient amount of piperazium group" is about the amount of equal mole.

The calcium hydroxide fulfills the dual role, which functions as the alkaline catalyst for hydrolyzing the ester and supplies the calcium ions for forming the semi-calcium salt, and proceeds the neutralization with the HCl of the KMUP-1 HCl salt respectively, to generate one or two molecular of the precipitation of the KMUP-1-Statinic acid. The statin derivative that does not react completely with KMUP-1 is dissolved in the hydrated alcohol solution. In the process of the present invention, the state of the reaction is monitored by Thin Layer Chromatography (TLC) and the developing solvent is MeOH:Ethyl acetate=1:9.

The excess amount of KMUP-1 HCl salt is required to react with the alginate sodium, the γ-polyglutamic acid, the sodium polyglutamate and the calcium polyglutamate-alginate sodium so as to complete the reaction and to synthesize the sodium-removable products. The un-crystallized KMUP-1

HCl salt is dissolved in the filtrate in the hydrated alcohol solution after the precipitation is filtered.

The synthesis of monoquarternary piperazium complex salt is performed by mixing the solution of $C_1$-$C_4$ lower alcohol and water, and the amount of the mixed solution is sufficient to dissolve the reactant. The "RX" moiety of reactant has a carboxyl group of a statin, the ester derivative of a statin, a statin derivative with the protecting group, the alginate sodium, the γ-polyglutamic acid, the sodium polyglutamate, the calcium polyglutamate-alginate sodium, repaglinide and nateglinide, montelukast, cromolyn sodium, nedocromil, gemfibrozil and bezafibrate. The $C_1$-$C_4$ lower alcohol is chosen and the amount of the mixed solution is adjusted upon factors such as the proportion of water, the reacting temperature and the purity of the statin ester derivative. Preferred alcohols are ethanol and isopropyl alcohol (IPA) and a preferred solvent mixture contains about 5% to 30% water in ethanol or IPA, more preferably about 10% water and about 90% ethanol (v/v) or IPA. The statin ester derivative is hydrolyzed in the alkaline catalyst, and which is added in the mixed solution in an amount about 10 mmoles $L^{-1}$ to about 1 mole $L^{-1}$. The temperature of the mixing solution should be heated to about 40° C. to 70° C. in a sequence to reflux the mixed solution for accelerating the reaction. The resulting KMUP-1 monoquarternary piperazium complex salt should be re-dissolved in another mixing solution after filtration, and preferably being re-crystallized under room temperature.

The trialkylsilyl group is a preferred silyl protecting group, which is hydrolyzed through the calcium hydroxide (PH 8.3). After being reacted with the calcium hydroxide, the silyl group may show a hydrolysis and being removed. Therefore, the protection of the silyl group can be removed and an ester structure is formed under a calcium salt. The above catalyzation by the mineral acid may be accomplished by hydrolyzing the protecting group with an acid, the adequate acids include the acetic acid, the trifluoroacetic acid, the p-toluenesulfonic acid, the zinc bromide and the hydrochloric acid or other hydrohalides, wherein the acetic acid and the hydrochloric acid are preferred.

The related drug in the present invention used in the human immune system refer to the non-steroid anti-inflammatory drugs (NSAIDs), the prostacyclin and the anti-asthmatic drug that contain a carboxyl group. Such NSAIDs containing a carboxyl group usually have a carboxyl group in the structure, such as aspirin, salicylic acid, indomethacin, diclofenac, meclofenamic acid, tolmetin, ketoprofen, methotrexate, flurbiprofen, fenoprofen, tiaprofen, diflunisal, etodolac, ibuprofen, prostacyclin and the commercial products such as montelukast, cromolyn sodium and nedocromil may also be employed. The above drugs directly react with the KMUP or piperazine compounds to form KMUP or monoquaternary piperazium salt. The sodium hydroxide, the potassium hydroxide, the calcium hydroxide or other metallic hydroxide and the ammonium hydroxide may also be utilized to form the salts of the NSAIDs, which then react with the KMUP HCl salt or piperazium HCl salt and form a complex salt. The commercial products of the anti-asthma or anti-allergy drug are such as montelukast, cromolyn sodium and nedocromil. The anti-allergy drug may show the anti-allergy effect via the antagonism of the leucotriene-D4 (LT-D4) receptor or other routes. The lipid-lowering fibric acid derivatives include gemfibrozil and fenofibrate, which can combine with the KMUP as a complex salt by using their carboxylic group, as well as the fibric acid. Besides, all of the alginate sodium, the γ-polyglutamic acid, the sodium polyglutamate and the calcium polyglutamate-alginate sodium for treating the diabetes, and the anti-diabetic drug containing the carboxylic group such as repaglinide and nateglinide, may react with the sufficient amount of the piperazium group of the KMUP or piperazine as the statin with the "RX" group to form the KMUP or piperazine-based monoquaternary piperazium complex salt. The reactants that can react with KMUP such as the "RX" group or the derivatives thereof are shown in FIGS. 2A-2C. The KMUP or piperazine-based monoquaternary piperazium complex salt with 1 or 4 single bond is formed depending upon the various reactants, and shows the pro-drug and the multiple therapeutic functions.

The present invention provides a mineral acid and organic acid salts of the KMUP-1 or piperazine, which may become a pharmaceutical composition by adding the statin and excipients. While being administered in the body of a mammal, it shows the pro-drug and the multiple therapeutic functions and lowers the risk of the above side effects. Therefore, the commercial products with the "RX" group may form a pharmaceutical composition by adding the excipient and KMUP or piperazine-based mineral acid salt or organic acid salt. For example, the commercial products with the "RX" group are statin (atorvastatin, cerivastatin, fluvastatin, lovastatin, mevastatin, pravastatin, rosuvastatin and simvastatin) and the NSAIDs (aspirin, salicylic acid, indomethacin, diclofenac, meclofenamic acid, tolmetin, ketoprofen, methotrexate, flurbiprofen, fenoprofen, tiaprofen, diflunisal, etodolac, ibuprofen or pro stacyclin, or the anti-asthma drugs (montelukast, cromolyn sodium and nedocromil), or the lipid-lowering drugs (gemfibrozil and fenofibrate), or the anti-diabetic drugs (alginate sodium, γ-polyglutamic acid, sodium polyglutamate, calcium polyglutamate-alginate sodium, repaglinide and nateglinide). The above-mentioned alginate sodium exists in the natural product of the brown algae, and the molecular chain thereof contains two structural units, the α-1,4-L-guluronic acid and β3-1,4-d-mannuronic acid. The γ-polyglutamic acid is referred as γ-PGA (1,2).

The above excipients or the phrases "pharmaceutically acceptable carrier or excipients" and "bio-available carriers or excipients" include any appropriate compounds known to be used for preparing the dosage form, such as the solvent, the dispersing agent, the coating, the anti-bacterial or anti-fungal agent and the preserving agent or the delayed absorbent. Usually, such kind of carrier or excipient does not have the therapeutic activity itself Each formulation prepared by combining the derivatives disclosed in the present invention and the pharmaceutically acceptable carriers or excipients will not cause the undesired effect, allergy or other inappropriate effects while being administered to an animal or human. Accordingly, the derivatives disclosed in the present invention in combination with the pharmaceutically acceptable carrier or excipients are adaptable in the clinical usage and in the human. A therapeutic effect can be achieved by using the dosage form in the present invention by the local or sublingual administration via the venous, oral, and inhalation routes or via the nasal, rectal and vaginal routes. About 0.1 mg to 100 mg per day of the active ingredient is administered for the patients of various diseases.

The carrier is varied with each formulation, and the sterile injection composition can be dissolved or suspended in the non-toxic intravenous injection diluents or solvent such as 1,3-butanediol. Among these carriers, the acceptable carrier may be mannitol or water. Besides, the fixing oil or the synthetic glycerol ester or di-glycerol ester is the commonly used solvent. The fatty acid such as the oleic acid, the olive oil or the castor oil and the glycerol ester derivatives thereof, especially the oxy-acetylated type, may serve as the oil for preparing the injection and as the naturally pharmaceutical acceptable oil. Such oil solution or suspension may include the long chain alcohol diluents or the dispersing agent, the carboxylmethyl cellulose or the analogous dispersing agent. Other carriers are common surfactant such as Tween and Spans or other analogous emulsion, or the pharmaceutically acceptable solid, liquid or other bio-available enhancing agent used for developing the formulation that used in the pharmaceutical industry.

The composition for oral administration adopts any oral acceptable formulation, which includes capsule, tablet, pill, emulsion, aqueous suspension, dispersing agent and solvent. The carrier generally used in the oral formulation, taking the tablet as an example, the carrier may be the lactose, the corn starch and the lubricant, and the magnesium stearate is the basic additive. The diluents used in the capsule include the lactose and the dried corn starch. For preparing the aqueous suspension or the emulsion formulation, the active ingredient is suspended or dissolved in an oil interface in combination with the emulsion or the suspending agent, and the appropriate amount of the sweetening agent, the flavors or the pigment is added as needed.

The nasal aerosol or inhalation composition may be prepared according to the well-known preparation techniques. For example, the bioavailability can be increased by dissolving the composition in the phosphate buffer saline and adding the benzyl alcohol or other appropriate preservative, or the absorption enhancing agent. The compound of the present invention may be formulated as suppositories for rectal or virginal administration.

The compound of the present invention can also be administered intravenously, as well as subcutaneously, parentally, muscular, or by the intra-articular, intracranial, intra-articular fluid and intra-spinal injections, the aortic injection, the sterna injection, the intra-lesion injection or other appropriate administrations.

Other objects, advantages and efficacies of the present invention will be described in detail below taken from the preferred embodiments with reference to the accompanying drawings, in which:

DETAILED DESCRIPTION OF THE PREFERRED EMBODIMENT

Figure 1:
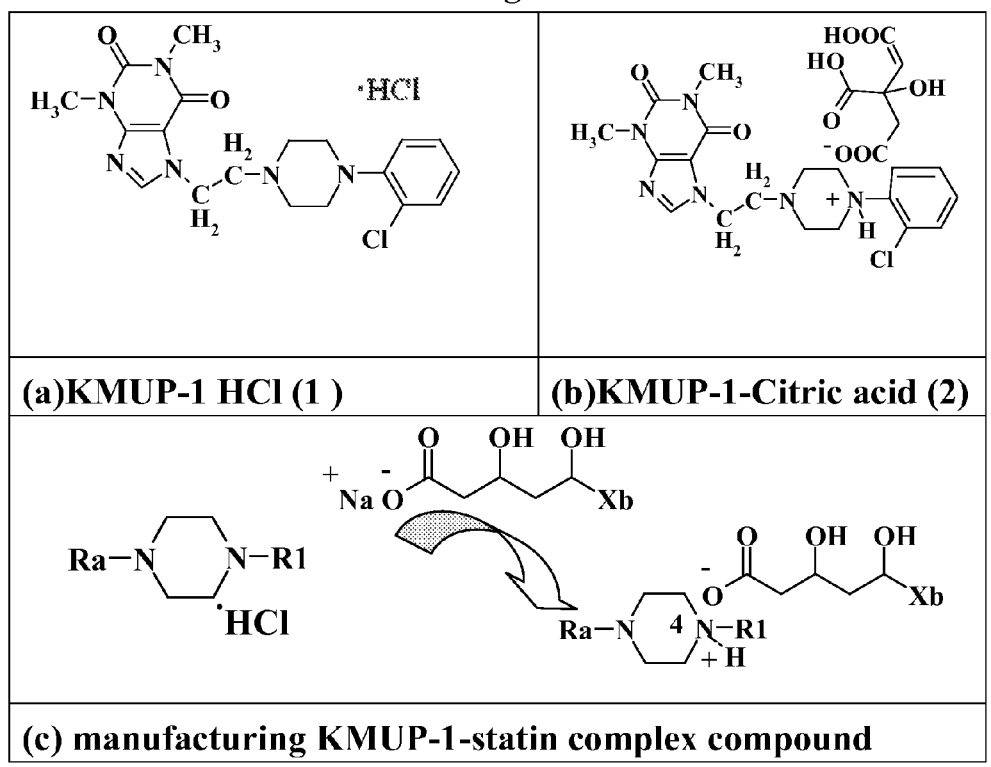
FIG. 1 shows the structures of: (a) KMUP-1 HCl salt (1), (b) KMUP-1 citric acid salt (2) and (c) KMUP-1-statin complex.
Figure 2A:
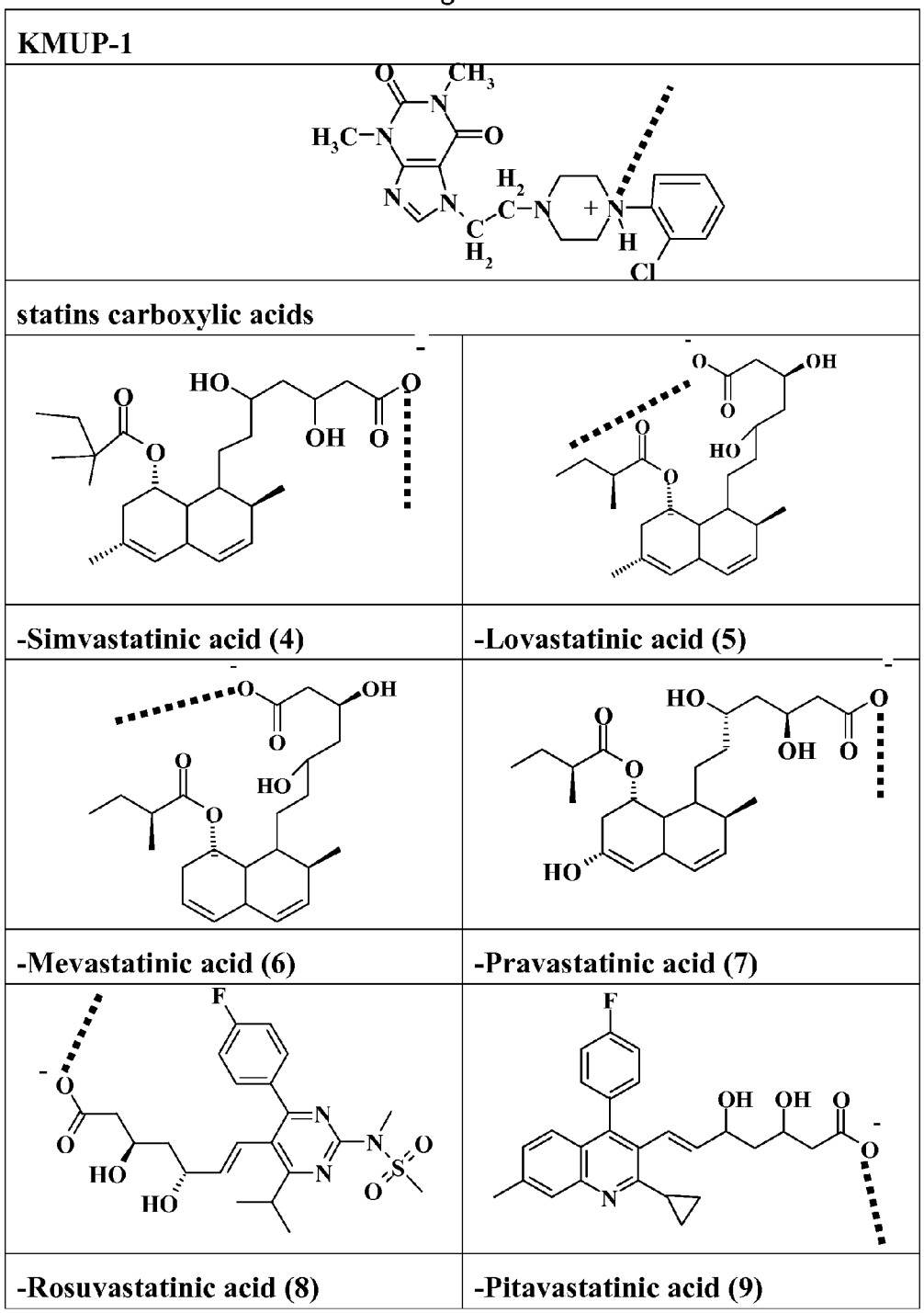
FIGS. 2A-2C show the structures of the KMUP-1 monoquarternary piperazium salts (3-18, 22).
Figure 2B:
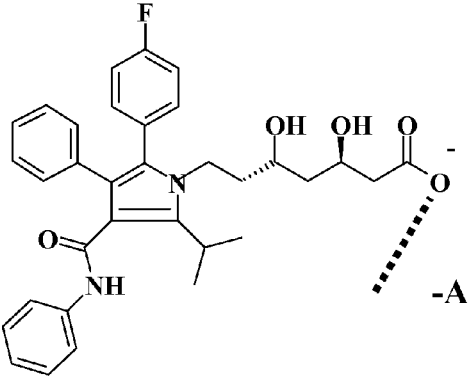
Figure 2C:
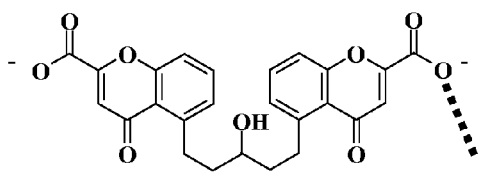
Figure 2C:
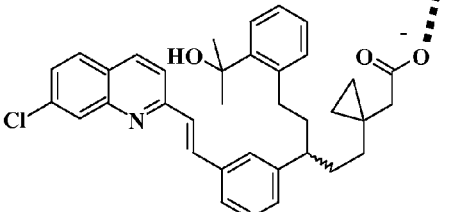
Figure 2C:
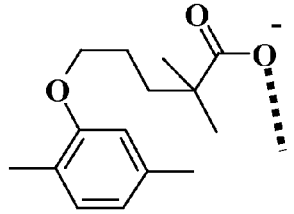
Figure 2C:
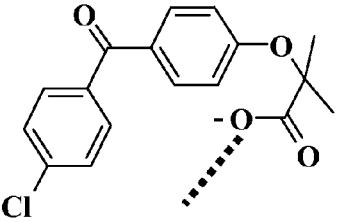
Figure 2C:
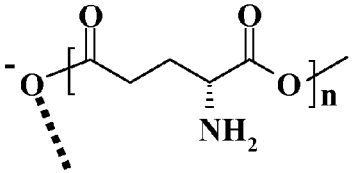
Figure 3:
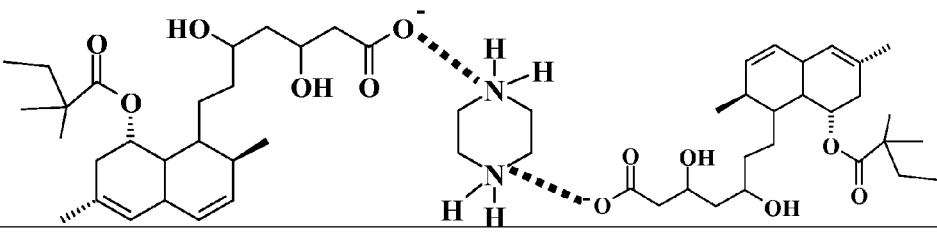
FIG. 3 shows the structures of the piperazine monoquarternary piperazium salts (19~21), KMUP-3 HCl salt (24) and KMUP-2 HCl salt (25).
Figure 3:
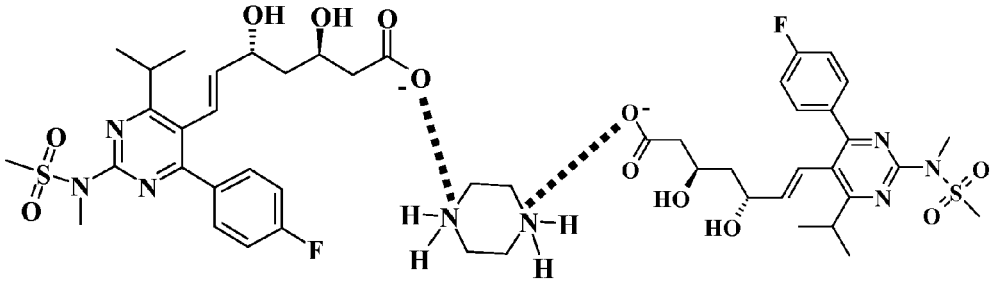
Figure 3:
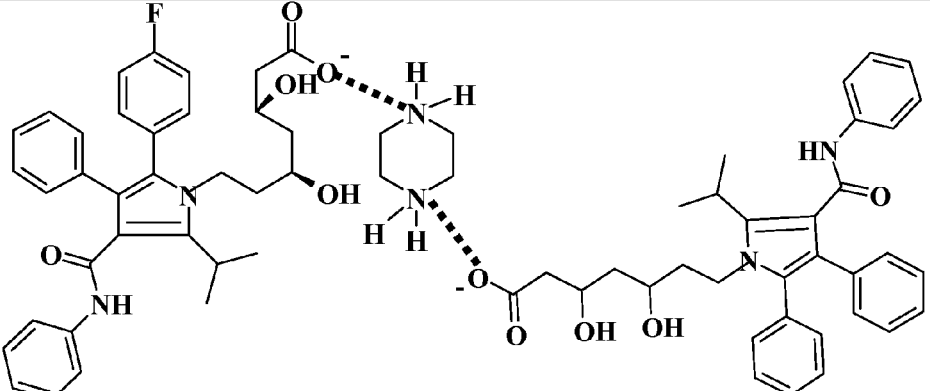
Figure 3:
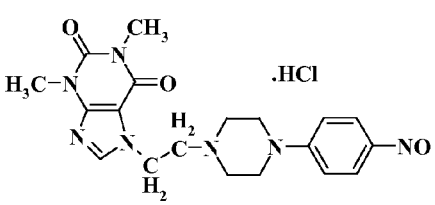
Figure 3:
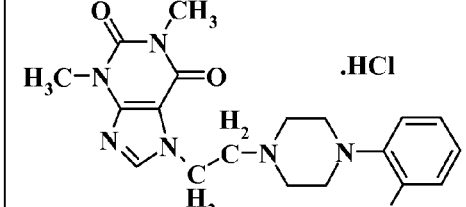

The KMUP or piperazine-based monoquarternary piperazium complex salts with 1 or 4 single bond prepared according to the embodiments in the present invention are shown as FIGS. 2A-3. The complex salts show lipid-lowering effect (Table 2), the effect on treating diabetes (Tables 3-5), anti-aggregation effect (Table 6), effect on lowering pulmonary hypertension (Tables 7-8), effect on inhibiting prostatic hyperplasia (Table 9), effect on inhibiting the growth of H1N1 virus (Table 10), effect on inhibiting growth of cancer cells (Table 11) and effect on inhibiting the asthma in animal (Table 12) in the following activity assay. Such assays illustrate that the KMUP or piperazine-based monoquaternary piperazium complex salt may show the multiple therapeutic functions of the commercial products with the "RX" group such as the statin, the NSAIDs, the anti-diabetic drugs, the anti-asthma drugs, the prostacyclin or the lipid-lowering drugs.

Therefore, the present invention is truly a rare novel invention and industrial applicable. Additionally, any modification may be practiced without leaving the scope of the appended claims by one of skill in the art.

The present application "PROCESSES FOR PREPARING PIPERAZINIUM SALTS OF KMUP AND USE THEREOF" will be fully understood from the following embodiments, and thereby being accomplished based thereon by one skilled in the art. However, the practice of the present application is not intended to limit to the following embodiments in its practice, and the skilled person can still conduct other embodiments according to the spirit of embodiments presented herein that belong to the scope of this invention.

Experimental Materials And Methods
Activity Assay
  1.The lipid-lowering effect in C57BL/6J mice
  8-week C57BL/6J mice are divided into standard diet (STD) group and the high-fat diet (HFD) group. In the HFD group, the KMUP-1 HCl salt (1, 2.5 and 5 mg/kg), the simvastatin (5 mg/kg), the KMUP-1-Nicotinic acid complex (1 and 5 mg/kg), the KMUP-1-Simvastatinic acid complex (1 and 5 mg/kg), KMUP-1-Gemfibrozil complex (2.5 mg/kg), KMUP-1-Fibric acid complex (2.5 mg/kg), KMUP-1-γ-polyglutamic acid complex (2.5 mg/kg) and KMUP-1-Citric acid complex (2.5 mg/kg) are administered orally. After 21 days, the amounts (mg/dl) of the triglyceride (TG), the total cholesterol (tot.-C), the high density lipoprotein cholesterol (HDL-C), the low density lipoprotein cholesterol (LDL-C) and the serum glucose of six mice for each group are measured as shown in Tables 2 and 3.

TABLE 2

The lipid-lowering effect in C57BL/6J mice

|  | TG | tot.-C | HDL-C | LDL-C |
|---|---|---|---|---|
| STD | 107.2 ± 6.1 | 78.67 ± 1.9 | 60.44 ± 1.6 | 6 ± 0.3 |
| HFD | 166.8 ± 5.3 | 166.8 ± 13.4 | 68.4 ± 3.5 | 31.33 ± 7 |
| KMUP-1 HCl salt (2.5 mg/kg) | 74.5 ± 5.1 | 133 ± 5.1 | 103.55 ± 4.2 | 14.17 ± 1.4 |
| KMUP-1 HCl salt (5 mg/kg) | 72.67 ± 4.7 | 125.5 ± 9.8 | 118.32 ± 5.7 | 14.2 ± 2.2 |
| Simvastatin (5 mg/kg) | 82.67 ± 6.3 | 133.67 ± 4.3 | 103.18 ± 2.5 | 15.3 ± 1.3 |
| KMUP-1-Nicotinic acid (5 mg/kg) | 80.75 ± 7.9 | 130 ± 4.1 | 97.98 ± 3.4 | 13.8 ± 1.2 |
| KMUP-1-Simvastatinic Acid (5 mg/kg) | 81.2 ± 4.4 | 129.7 ± 1.4 | 108.4 ± 1.3 | 17.3 ± 1.4 |

TABLE 2-continued

The lipid-lowering effect in C57BL/6J mice

|  | TG | tot.-C | HDL-C | LDL-C |
|---|---|---|---|---|
| KMUP-1-Citric acid (2.5 mg/kg) | 83.2 ± 5.3 | 129.7 ± 1.6 | 108.4 ± 1.3 | 16.4 ± 1.7 |
| KMUP-1-Gemfibrozil (2.5 mg/kg) | 79.2 ± 4.6 | 130.7 ± 1.7 | 98.7 ± 1.8 | 18.2 ± 1.8 |
| KMUP-1-Fibric acid (2.5 mg/kg) | 80.2 ± 3.2 | 132.7 ± 1.3 | 98.4 ± 1.3 | 18.4 ± 2.2 |
| KMUP-1-γ-polyglutamic acid (2.5 mg/kg) | 78.2 ± 3.6 | 129.4 ± 1.4 | 97.3 ± 1.6 | 16.5 ± 0.9 |

TABLE 3

The amount of the serum glucose in C57BL/6J mice

|  | The amount of serum glucose (mg/dl) | The amount of serum insulin (mg/dl) |
|---|---|---|
| Standard diet | 105.6 ± 3.6 | 0.79 ± 0.14 |
| HFD | 151.2 ± 4.2 | 2.97 ± 0.36 |
| HFD + KMUP-1 HCl salt (1 mg/kg) | 120.4 ± 4.2 | 0.91 ± 0.24 |
| HFD + KMUP-1-Simvastatinic Acid (1 mg/kg) | 117.3 ± 3.8 | 0.85 ± 0.17 |
| HFD + KMUP-1-Nicotinic acid (1 mg/kg) | 123.5 ± 2.5 | 0.89 ± 0.42 |

TABLE 4

The amount of the serum glucose in STZ-induced diabetic rats

|  | The amount of the serum glucose (mg/dl) | Body weight (g) |
|---|---|---|
| Standard group | 100 ± 12.3 | 248.6 ± 1.6 |
| STZ group | 373.1 ± 17.3 | 284.2 ± 16.4 |
| STZ + KMUP-1 HCl salt (0.5 mg/kg) | 215.4 ± 19.6 | 312.2 ± 8.9 |
| STZ + KMUP-1 HCl salt (1.5 mg/kg) | 215.4 ± 23.8 | 310.2 ± 7.4 |
| STZ + KMUP-1 HCl salt (2.5 mg/kg) | 210.4 ± 15.7 | 308.2 ± 8.4 |
| STZ + KMUP-1 HCl salt (5 mg/kg) | 200.2 ± 14.2 | 301.3 ± 11.7 |
| STZ + KMUP-1-Simvastatinic acid (5 mg/kg) | 194.2 ± 16.1 | 311.2 ± 12.6 |

2. The effect of KMUP-1 on decreasing the amount of the serum glucose in streptozosin (STZ)-induced diabetic rats 60 mg/kg of streptozosin is injected intravenously for inducing the STZ-induced rats, and the KMUP-1 HCl salt (0.5, 1.5, 2.5 and 5 mg/kg) and KMUP-1-Simvastatinic acid (5 mg/kg) are administered orally. After 21 days, the amount of the serum glucose (mg/dl), the amount of the serum insulin (mg/dl), the body weight (g) and the change of the body weight are measured.

3. Administering KMUP-1 and the complex salts after meal shows a synergic effect of the amounts of the serum glucose and insulin.

Nateglinide, repaglinide or the placebo is administered on day 1 before one hour of the breakfast, and the KMUP-1/ KMUP-1-Nateglinide or KMUP-1-Repaglinide are orally administered at 1, 2, 3, 4, 5 and 6 hrs respectively. The amount of the serum glucose (mg/dl), the amount of the serum insulin (mg/dl), the body weight (g) and the change of the body weight are measured.

TABLE 5

The amount of the serum glucose in STZ-induced diabetic rats

|  |  | The change of the insulin after administration (U/mL) | | | | | The change of the fasting blood glucose after administration (mg/dl) | | |
|---|---|---|---|---|---|---|---|---|---|
| (mg/kg) |  | 1 hr | 2 hr | 3 hr | 4 hr | 6 hr | 1 hr | 2 hr | 6 hr |
| STZ control group |  | 15.7 ± 2.6 | 18.4 ± 1.7 | 11.6 ± 2.4 | 6.2 ± 1.5 | 1.4 ± 0.8 | 1.6 ± 0.8 | 1.8 ± 0.6 | −0.4 ± 0.3 |
| KMUP-1 HCl salt | 1 | 10.1 ± 1.8 | 16.4 ± 2.2 | 12.6 ± 2.4 | 6.7 ± 2.4 | 1.8 ± 0.7 | 3.7 ± 0.6* | 2.3 ± 0.7 | 0.1 ± 0.5 |
|  | 2 | 26.4 ± 1.3* | 30.6 ± 4.6* | 13.8 ± 3.6* | 9.5 ± 1.7* | 4.6 ± 0.8* | 4.3 ± 0.4* | 2.5 ± 0.2 | 0.3 ± 0.7 |
|  | 3 | 38.2 ± 3.8* | 32.6 ± 6.4* | 21.4 ± 2.6* | 18.4 ± 2.4* | 7.4 ± 3.6* | 5.2 ± 0.9* | 1.7 ± 0.1 | −0.1 ± 0.3 |
|  | 4 | 37.4 ± 3.6* | 47.3 ± 2.3* | 27.8 ± 2.8* | 14.8 ± 3.7* | 2.8 ± 0.5 | 5.7 ± 0.8* | 1.5 ± 0.2 | −0.3 ± 0.1 |
| KMUP-1-Nat (4) |  | 38 ± 2.7* | 51.3 ± 4.3* | 31.8 ± 3.7* | 21.8 ± 5.3* | 3.4 ± 0.6* | 4.67 ± 0.7 | 0.8 ± 0.4 | −0.2 ± 0.3 |
| KMUP-1-Rep (4) |  | 39.5 ± 3.8* | 47.3 ± 2.2* | 27.4 ± 2.8 | 14.8 ± 3.7* | 2.8 ± 0.5 | 5.7 ± 0.8 | 0.5 ± 0.2 | −0.3 ± 0.1 |
| Nat (4) |  | 42.5 ± 4.2* | 49.3 ± 3.4 | 24.4 ± 4.6* | 17.8 ± 2.8* | 4.4 ± 0.6* | 4.7 ± 0.6 | 0.3 ± 0.2 | −0.2 ± 0.3 |
| Rep (4) |  | 47.5 ± 3.7* | 49.3 ± 3.4* | 24.4 ± 4.6* | 19.8 ± 3.6* | 4.8 ± 0.4* | 3.2 ± 0.8 | 0.6 ± 0.1 | −0.1 ± 0.4 |

*P < 0.05, which represents the significant difference in comparison with the STZ control group.
Nat (Nateglinide), KMUP-1-Nat (KMUP-1-Nateglinide),
Rep (Repaglinide), KMUP-1-Rep (KMUP-1-Repaglinide).

4. The rabbit serum shows the antiplatelet aggregation activity

The blood of the rabbit marginal ear vein is collected and added ethylene diamine-N,N-tetraacetic acid (EDTA) to make the final concentration as 6 mmol/L. After centrifuging at 90 s for 10 mins, the supernatant is platelet-rich plasma (PRP). The platelet suspension is obtained from EDTA-anticoagulated PRP, and the platelet granules are finally suspended in the Tyrode's solution. Each liter of Tyrode's solution contains the following components (millimoles): sodium chloride (136.8), potassium chloride (2.8), sodium bicarbonate (1.1), magnesium chloride (2.1), sodium dihydrogen phosphate (0.33), calcium chloride (1.0), glucose (1.2) and bovine serum albumin (0.35%). The turbidity is measured at 37° C. by Lumi-aggregometer connected with two dual channel recorders as the aggregation. The platelets are stirred at 1200 rpm to eliminate the influence of the solvent, which is fixed with dimethyl sulfoxide (DMSO) in 0.6% (vol/vol) at the final concentration. The activities for inhibiting the U46619-induced platelet aggregation of the indomethacin and the complex salts such as KMUP-1 HCl salt (n=8) are tested.

TABLE 6

The activity of antiplatelet aggregation

|  | The concentration of PRP (µM) | The ratio of the antiplatelet aggregation (%) |
|---|---|---|
| Control group (U46619) | 1 |  |
| U46619 + Indomethacin | 20 | 87 ± 8.3* |
| U46619 + KMUP-1 HCl salt | 20 | 89 ± 3.4* |
| U46619 + KMUP-1-Indomethacin | 20 | 92 ± 5.8* |
| U46619 + KMUP-1-Citric acid | 20 | 78 ± 2.7* |

*$P < 0.05$, which represents the significant difference in comparison with the control group.

5. the monocrotaline (MCT)-treated rats show the decreased pulmonary aterial hypertension Pulmonary aterial hypertension in MCT-treated rats is caused on day 21 after the intraperitoneal injection. Orally administered KMUP-1 HCl salt (2.5 mg/kg), simvastatin (2.5 mg/kg), KMUP-1-nicotinic acid complex (2.5 mg/kg), KMUP-1-Citric acid complex (2.5 mg/kg), KMUP-1-Simvastatinic acid complex (2.5 mg/kg) and KMUP-1-γ-Polyglutamic acid complex (2.5 mg/kg), or the inhaled KMUP-1-PGI$_2$ (0.1 mM) every day may inhibit the male Wistar rats treated with MCT, which show the effect of decreasing the pulmonary artery blood pressure (PABP).

TABLE 7

Inhibition of the pulmonary artery blood pressure

| Group | Does (mg/kg/day) | PABP (mmHg) |
|---|---|---|
| Control group |  | 11 ± 1.4 |
| MCT (60 mg, intracutaneously) |  | 25 ± 2.3 |
| MCT + KMUP-1 HCl salt | 2.5 mg, p.o. | 13 ± 1.7 |
| MCT + KMUP-1-Citric acid | 2.5 mg, p.o. | 16 ± 1.8 |
| MCT + KMUP-1-Nicotinic acid | 2.5 mg, p.o. | 12 ± 2.6 |
| MCT + KMUP-1-Simvastatinic acid | 2.5 mg, p.o. | 12 ± 1.3 |
| MCT + KMUP-1-γ-Polyglutamic acid | 2.5 mg, p.o. | 11 ± 0.6 |
| MCT + KMUP-1-PGI$_2$ | 0.1 mM (inhalation) | 10 ± 0.2 |

6. KMUP-1 salts inhibit the lung fibrosis in mice induced by bleomycin (BM) mediated via transforming growth factor beta (TGF-β) expression in lung The increased amount of the synthetic collagen and the generation of the macrophage in alveolus may facilitate the formulation of TGF-β, and the expression of TGF-β is looked as a biomarker of the lung fibrosis. KMUP-1 HCl salt (1, 2.5 and 5 mg/kg), the simvastatin (5 mg/kg), the KMUP-1-nicotinic acid complex (2.5 mg/kg), the KMUP-1-Simvastatinic acid complex (2.5 mg/kg) and KMUP-1-γ-Polyglutamic acid complex (2.5 mg/kg) are orally administered to the mice for inhibiting the lung fibrosis induced by TGF-β expression in tracheal irrigation solution that resulted from 60 mg/kg BM inhalation (Table 7). The state of the TGF-β expression in the irrigation solution is measured by the enzyme immunoassay (EIA).

TABLE 8

The inhibition of lung fibrosis

| Drug (mg/kg) Bleomycin (BM, 60) | Changing % of the lung TGF-β |
|---|---|
| BM + Simvastatin (5) | 40 ± 4.3* |
| BM + KMUP-1 HCl salt (2.5) | 52 ± 5.2* |
| BM + KMUP-1-Simvastatinic acid (2.5) | 45 ± 4.5* |
| BM + KMUP-1-Nicotinic acid (2.5) | 42 ± 3.8* |
| BM + KMUP-1-γ-Polyglutamic acid (2.5) | 42 ± 1.6* |

*$P < 0.05$, which represents the significant difference in comparison with the control group.

7. KMUP-1 salts inhibit the prostate hypertrophy (BPH) in testosterone-induced mice The testosterone (TS, 3 mg/kg/day) is administered for 4 weeks for inducing BPH in mice, which combines with KMUP-1 HCl salt (2.5 mg/kg), KMUP-1-Citric acid (2.5 mg/kg) and KMUP-1-Nicotinic acid (2.5 mg/kg), and the ratio of hypertrophy (g)/body weight (g) is measured at day 28 (n=6).

TABLE 9

Inhibition of BPH in TS-induced mice

| Drug (mg/kg) | hypertrophy (g)/ body weight (g) |
|---|---|
| Control group | 0.19 ± 0.02 |
| Testosterone (TS, 3) | 0.32 ± 0.03 |
| TS + KMUP-1 HCl salt (2.5) | 0.21 ± 0.04* |
| TS + KMUP-1-Citric acid (2.5) | 0.23 ± 0.05* |
| TS + KMUP-1-Nicotinic acid (2.5) | 0.19 ± 0.07* |

*$P < 0.05$, which represents the significant difference in comparison with the control group.

8. Inhibition of the growth of H1N1 virus

After the mardin darby canine kidney (MDCK) culture is infected with H1N1 virus, KMUP-1 HCl salt or KMUP-1-Simvastatinic acid in the glucose solution is administered. It is found that such administration can inhibit the growth of the virus (n=6).

TABLE 10

Inhibition of the growth of H1N1 virus

| Drug | IC$_{50}$ (µg/ml) |
|---|---|
| KMUP-1 HCl salt | 5.2 |
| KMUP-1-Simvastatinic acid | 1.8 |
| KMUP-1-Lovastatinic acid | 1.9 |
| KMUP-1-Pravastatinic acid | 2.1 |

9. Inhibition of the growth of cancer cells

The cytotoxicity of KMUP-1 HCl salt and KMUP-1-Methotrexate (KMUP-1-MTX) in glucose solution (5%) to L1210 leukemia cell line (n=6) are tested by the diphenyltetrazolium bromide (MTT) assay. The methotrexate (MTX) is served as the positive control group. Briefly, the cancer cells (5000-10000 cells/ml) is added together with the compounds to be tested into each well of 96-well plate. After culturing for 3 days, the attached cells are cultured in MTT (0.5 mg/ml) for one hour, followed by dissolving the formazan crystal with dimethyl sulfoxide (DMSO). The absorption at 550 nm wave length is measured by the enzyme linked immunosorbent assay (ELISA) reader. IC50 is the concentration of the tested compound for inhibiting 50% cell growth under the experimental conditions.

TABLE 11

Inhibition for the growth of the cancer cells

| Drug | $IC_{50}$ (nM) |
| --- | --- |
| MTX | 12 |
| KMUP-1 HCl salt | 26 |
| KMUP-1-MTX | 20 |

10. Inhibition of the asthma in animals

The ovalbumin (OVA, 5 mM, 30 mins) is intraperitoneally injected into male BALB/c mice (20~23 g). After being sensitized with intraperitoneally injected OVA on day 1 and day 8 to reaveal the asthma animals, the asthma is induced by aluminum hydroxide (2 mg) aerosol attached with 10 μg OVA. The aerosol of 5 mM/30 mins/day KMUP-1 HCl salt or the related complex salts are administered on day 21 to 27. The asthma animals are divided into 5 groups where the control group is administered the saline aerosol only and other experimental groups are administered 1% OVA aerosol followed by the aerosol of the related complex salts as shown in Table 12. The expression of the inhibited matrix metalloprotease-9 (MMP-9) induced by OVA in lung tissue of BALB/c mice is measured.

TABLE 12

Inhibition of MMP-9 in lung tissues of mice

| Drug 5 mM | Inhibition (%) |
| --- | --- |
| OVA + Vehicle Control | 0 |
| OVA + KMUP-1 HCl salt | 55 ± 3.5 |
| OVA + KMUP-1-Cromolyn | 60 ± 4.4 |
| OVA + KMUP-1-Nedocromil | 63 ± 3.8 |
| OVA + KMUP-1-Montelukast | 70 ± 5.2 |

($p < 0.01$; N = 6, significantly different from control group)

11. Treatment of osteoporosis by inhibiting osteoclast differentiation demonstrated by RAW 264.7 cells Cell-to-cell contact between osteoblasts (or bone marrow stroma cells) and osteoclast precursors is required for osteoclast formation. Some of the proteins involved in the interaction between cells of osteoblastic and osteoclastic lineage. These proteins belong to the families of tumor necrosis factors (TNFs) and receptors. Receptor activator of nuclear factor-κB ligand (RANKL), a protein expressed on the osteoblast cell membrane, binds to receptor activator of nuclear factor-κB (RANK), a receptor located on the osteoclast membrane, resulting in activation and differentiation of osteoclasts. Inhibition of either RANKL or RANK interrupts RANKL-RANK signaling between osteoblasts and immature osteoclasts causes a lack of functioning mature osteoclasts and thus reduce bone resorption. RAW 264.7 cell is looked as the representation of hematopoietic monocyte/macrophage of osteoclastic lineage.

Effects of KMUP-1, statin and KMUP-1-statinic acid complex treatment on the expression levels of osteoclast differentiation marker, a fluorescence-based staining for tartrate-resistant acidic phosphatase (TRAP), were monitored in RAW 264.7 cells that have osteoclastic activity induced by combining RANKL (10 μg/ml) with cells on a slice in the presence of KMUP-1, statins and KMUP-1-statinic acid at 5 μM for 5 days culturing. The slices were stained with bleach solution and observed under a light microscope. KMUP-1, statin and complex combinations suppressed the TRAP-positive cell count caused by RANKL.

TABLE 13

Inhibition of the osteoclast differentiation (TRAP-Positive Cell counts)

| Drug 5 μM | TRAP-Positive Cells |
| --- | --- |
| RANKL + Vehicle Control | 500 ± 12 |
| RANKL + KMUP-1 HCl salt | 80 ± 6 |
| RANKL + Simvastatin | 85 ± 7 |
| RANKL + KMUP-1-Simvastatinic acid | 72 ± 5 |
| RANKL + KMUP-1-Lovastatinic acid | 73 ± 6 |
| RANKL + KMUP-1-Atorvastatinic acid | 78 ± 3 |

All values are significantly different from Vehicle control ($p < 0.01$; n = 5)

EXAMPLES

Statinic acid indicates the open-lactone type statin having the carboxylic acid moiety. For example, simvastatinic acid indicates that simvastatin chemically with the carboxylic acid moiety. Atorvastatinic acid, rosuvastatinic acid, lovastatinic acid and other statinic acid indicate that atorvastatin, rosuvastatin and lovastatin chemically with the carboxylic acid moiety.

Example 1

Preparation of KMUP-1 HCl Salt (7-[2-[4-(2-chlorobenzene)piperazinyl]ethyl]-1,3-dimethyl xanthine HCl, 1)

KMUP-1 (8.0 g) is dissolved in a mixture of ethanol (10 mL) and HCl (1 N, 60 mL) the solution is reacted at 50° C. for 20 mins, the methanol is added thereinto under room temperature and the solution is incubated over night for crystallization and filtrated to obtain KMUP-1 HCl salt (7.4 g).

Example 2

Preparation of KMUP-1-Citric Acid Salt (2)

KMUP-1 (8.0 g) is dissolved in a mixture of ethanol (10 mL) and citric acid (4 g) and reacted at 50° C. for 20 min, the methanol is added thereinto under room temperature and the solution is incubated over night for crystallization and filtrated to obtain KMUP-1-Citric acid salt (10.5 g).

Example 3

Preparation of KMUP-1-Nicotinic Acid Salt (3)

KMUP-1 (8.0 g) is dissolved in a mixture of ethanol (10 mL) and nicotinic acid (2.4 g) and reacted at 50° C. for 20 min, the methanol is added thereinto under room temperature and the solution is incubated over night for crystallization and filtrated to obtain KMUP-1-Nicotinic acid salt (8.3 g).

Example 4

Preparation of KMUP-1-Simvastatinic Acid Complex (4)

KMUP-1 (8.0 g) is dissolved in a mixture of ethanol (10 mL) and HCl (1 N, 60 mL) and reacted at 50° C. for 10 min, the methanol is added thereinto under room temperature and the solution is incubated over night for crystallization and filtrated to obtain KMUP-1 HCl (7.4 g). Take KMUP-1 HCl salt (4.4 g) and redissolve it in ethanol (150 mL) for use.

In a flask equipped with a magnetic stirrer, simvastatin (4.2 g) dissolved in ethanol (50 ml) is poured, to which an aqueous solution of sodium hydroxide (4 g/60 ml) and the above-mentioned filtrate of KMUP-1 HCl salt reacted with the ethanol are added under room temperature. The mixture is reacted at 50° C. for 20 mins, rapidly filtrated and incubated one hour for crystallization to give the KMUP-1-Simastatinic acid complex.

Example 5

Preparation of KMUP-1-Lovastatinic Acid Complex (5)

KMUP-1 (8.0 g) is dissolved in a mixture of ethanol (10 mL) and HCl (1 N, 60 mL) and reacted at 50° C. for 10 min, the methanol is added thereinto under room temperature and the solution is incubated over night for crystallization and filtrated to obtain KMUP-1 HCl (7.4 g). Take KMUP-1 HCl salt (4.4 g) and redissolve it in ethanol (150 mL) for use.

In a flask equipped with a magnetic stirrer, lovastatin (4.2 g) dissolved in ethanol (50 ml) is poured, to which an aqueous solution of sodium hydroxide (4 g/60 ml) and then the above-mentioned filtrate of KMUP-1 HCl solution to react in ethanol, kept under room temperature. The mixture is warmed at 50° C. for 20 mins, rapidly filtrated for removing the resulted sodium chloride and then incubated one hour for crystallization to give the KMUP-1-Lovastatinic acid complex.

Example 6

Preparation of KMUP-1-Mevastatinic Acid Complex (6)

KMUP-1 (8.0 g) is dissolved in a mixture of ethanol (10 mL) and HCl (1 N, 60 mL) and reacted at 50° C. for 20 min, the methanol is added thereinto under room temperature and the solution is incubated over night for crystallization and filtrated to obtain KMUP-1 HCl (7.4 g). Take KMUP-1 HCl salt (4.4 g) and redissolve it in ethanol (150 mL) for use.

In a flask equipped with a magnetic stirrer, mevastatin (4 g) dissolved in ethanol (50 ml) is poured, to which an aqueous solution of sodium hydroxide (4 g/60 ml) is added under room temperature. After 10 mins, the above-mentioned KMUP-1 HCl salt in the ethanol solution is added for reacting at 50° C. for 20 mins, and the mixture is rapidly filtrated and incubated one hour for crystallization to give the KMUP-1-Mevastatinic acid complex.

Example 7

Preparation of KMUP-1-Pravastatinic Acid Complex (7)

KMUP-1 (8.0 g) is dissolved in a mixture of ethanol (10 mL) and 1N HCl (60 mL) and reacted at 50° C. for 20 min and cooled to room temperature, the ethanol is added thereinto and the solution is incubated over night for crystallization and filtrated to obtain KMUP-1 HCl (7.4 g). Take KMUP-1 HCl salt (4.4 g) and re-dissolve it in ethanol (150 mL) for use.

In a flask equipped with a magnetic stirrer, pravastatin sodium (4.5 g) dissolved in mixture of ethanol (50 ml) and water (50 ml) is poured. An aqueous solution of sodium hydroxide (4 g/60 ml) and the above-mentioned reacting solution of KMUP-1 HCl salt and the ethanol are added into the mixture under room temperature. The mixture is reacted at 50° C. for 20 mins, rapidly filtrated for removing sodium chloride and incubated one hour for crystallization to give the KMUP-1-Pravastatinic acid complex.

Example 8

Preparation of KMUP-1-Rosuvastatinic Acid Complex (8)

KMUP-1 HCl salt is prepared according to the procedures in the Examples 4-7.

In a flask equipped with a magnetic stirrer, rosuvastatin (10.5 g) dissolved in ethanol (150 mL) is added, to which an aqueous solution of sodium hydroxide (4 g/60 ml) and KMUP-1 HCl salt (4.4 g) dissolved in ethyl alcohol (150 ml) are added under room temperature. The mixture is stirred continuously at 50° C. for 20 minutes, concentrated under reduced pressure to 300 ml and filtered quickly for removing sodium chloride and cooling the filtrate to give precipitate of KMUP-1-Rosuvastatinic acid complex.

Example 9

Preparation of KMUP-1-Pitavastatinic Acid Complex (9)

KMUP-1 HCl salt is prepared according to the procedures in the Examples 4-7.

In a flask equipped with a magnetic stirrer, pitavastatin (8.8 g) dissolved in ethanol (100 mL) is poured thereinto, to which an aqueous solution of sodium hydroxide (4 g/60 ml) and the KMUP-1 HCl salt (4.4 g) dissolved in ethyl alcohol (150 ml) are added. The mixture is stirred at 50° C. for 20 minutes until the reaction is completed. The mixture is quickly filtered and then concentrated under reduced pressure. Water is added to the mixture after it is cooled, and stirring the mixture at room temperature for 20 mins until the reaction is completed. After filtering the precipitate, a white KMUP-1-Pitavastatinic acid complex is obtained.

Example 10

Preparation of KMUP-1-Atorvastatinic Acid Complex (10)

KMUP-1 HCl salt is prepared according to the procedures in the Examples 4-7.

In a flask equipped with a magnetic stirrer, atorvastatin (11.5 g) dissolved in ethanol (100 mL) is poured thereinto, to which an aqueous solution of sodium hydroxide (4 g/60 ml) and the KMUP-1 HCl salt (4.4 g) dissolved in ethyl alcohol (150 ml) are added. The mixture is stirred at 50° C. for 15 minutes until the reaction is completed. The mixture is quickly filtered and then concentrated under reduced pressure. Water is added to the mixture after it is cooled, and stirring the mixture at room temperature for 20 mins until the reaction is completed. After filtering the precipitate, a white KMUP-1-Atorvastatinic acid complex is obtained.

Example 11

Preparation of KMUP-1-Atorvastatinic Acid Complex

KMUP-1 HCl salt is prepared according to the procedures in the Examples 4-7.

In a flask equipped with a magnetic stirrer, atorvastatin calcium salt (13.6 g) suspended in a mixture of ethanol (100 ml) and water (30 ml) is poured. KMUP-1 HCl salt (4.4 g), dissolved in ethyl alcohol (150 ml) is added into the suspension under room temperature. The mixture is stirred continuously at 50° C. for 20 minutes until the reaction is completed. The mixture is filtered quickly and concentrated under reduced pressure. The mixture is then cooled to ambient temperature, after which, water is added. The mixture is stirred under room temperature for 20 minutes until the reaction is completed. After filtering the precipitate for removing sodium chloride, a white KMUP-1-Atorvastatinic acid complex is obtained.

Example 12

Preparation of KMUP-1-Methotrexate (MTX) Complex (11)

KMUP-1 (8 g) is dissolved in a mixture of ethanol (100 mL) and water (30 mL), to which MTX (9.8 g) dissolved in ethyl alcohol (150 mL) is added, and the mixture is reacted at 50° C. for 20 mins. After cooling to the room temperature, the resulting precipitate is dissolved by adding methanol, re-crystallized over night and then filtrated to obtain KMUP-1-MTX complex (15.3 g).

Example 13

Preparation of KMUP-1-Indomethacin Complex (12)

KMUP-1 (8.0 g) is dissolved in a mixture of ethanol (100 mL) and water (30 mL), to which indomethacin (7 g) dissolved in ethyl alcohol (150 mL) is added, and the mixture is reacted at 50° C. for 20 mins. The precipitate is obtained through filtering under room temperature, which is re-crystallized from methanol over night and then filtrated to obtain KMUP-1-Indomethacin complex (13.2 g).

Example 14

Preparation of KMUP-1-Repaglinide Complex (13)

KMUP-1 (8.0 g) is dissolved in a mixture of ethanol (100 mL) and water (30 mL), to which repaglinide (9.1 g) dissolved in ethyl alcohol (150 mL) is added, and the mixture is reacted at 50° C. for 20 mins. The precipitate is obtained through filtering under room temperature, which is re-crystallized from methanol over night at room temperature and then filtrated to obtain KMUP-1-repaglinide complex (15.3 g).

Example 15

Preparation of KMUP-1-Nateglinide Complex (14)

KMUP-1 (8.0 g) is dissolved in a mixture of ethanol (100 mL) and water (30 mL), to which nateglinide (9.1 g) dissolved in ethyl alcohol (150 mL) is added, and the mixture is reacted at 50° C. for 20 mins. After cooling the mixture, the white precipitate is obtained, to which the methanol is added under room temperature and being incubated over night for re-crystallization. After filtering, KMUP-1-nateglinide complex (15.3 g) is obtained.

Example 16

Preparation of KMUP-1-Cromolyn Complex (15)

KMUP-1 HCl salt (8.8 g) is dissolved in a mixture of ethanol (100 mL) and water (30 mL), to which cromolyn di-sodium (10.2 g) dissolved in ethyl alcohol (300 mL) is added and the mixture is reacted at 50° C. for 20 mins. After cooling to room temperature, the white precipitate is obtained, to which the methanol is added under room temperature and being incubated over night for re-crystallization. The crystal is filtered to obtain KMUP-1-Cromolyn mono-sodium complex (16.2 g).

Example 17

Preparation of KMUP-1-Montelukast Complex (16)

KMUP-1 HCl salt (8.8 g) is dissolved in a mixture of ethanol (100 mL) and water (30 mL), to which montelukast (11.7 g) dissolved in ethyl alcohol (300 mL) is added and the mixture is reacted at 50° C. for 20 mins. After cooling to room temperature, the white precipitate is obtained, to which the methanol is added under room temperature after the sodium chloride is removed and the reaction is incubated over night for re-crystallization. The crystal is filtered to obtain KMUP-1-montelukast complex (16.8 g).

Example 18

Preparation of KMUP-1-Gemfibrozil Complex (17)

The aqueous solution of sodium hydroxide (4 g/60 ml) is added into gemfibrozil (2.5 g) in ethanol (100 ml) under room temperature to result a gemfibrozil sodium solution for use.

KMUP-1 HCl salt (4.4 g) dissolved in ethanol (100 ml) is added the gemfibrozil sodium solution for reacting at 50° C. for 20 mins. After cooling to room temperature, the white precipitate is obtained and filtered for removing the sodium citric acid. The methanol is added to the precipitate under room temperature for re-crystallization over night, and the crystal is filtered to obtain KMUP-1-gemfibrozil complex (5.2 g).

Example 19

Preparation of KMUP-1-Fibric Acid Complex (18)

The aqueous solution of sodium hydroxide (4 g/60 ml) is added into Fenofibrate (3.6 g) in ethanol (100 ml) under room temperature to result a gemfibrozil sodium solution for use.

KMUP-1 HCl salt (4.4 g) dissolved in ethanol (150 ml) is added the fenofibric acid sodium solution for reacting at 50° C. for 20 mins. After cooling to room temperature, the white precipitate is obtained and filtered for removing the sodium citric acid. The methanol is added to the precipitate under room temperature for re-crystalization over night, and the crystal is filtered to obtain KMUP-1-fibric acid complex (5.6 g).

Example 20

Preparation of Di-Simvastatinic Acid Piperazinium Salt (19)

The aqueous solution of sodium hydroxide (4 g/60 ml) is added into simvastatin (8.4 g) in ethanol (100 ml) under room temperature to result a solution of simvastatinic acid di-sodium in ethanol for use.

Piperazine di-hydrochloride (1.6 g) dissolved in the mixture of ethanol (100 ml) and water (30 ml) is added a solution of simvastatinic acid di-sodium dissolved in the hydrous ethanol for reacting at 50° C. for 20 mins. After cooling to room temperature, a white precipitate is obtained and filtered for removing the sodium hydrochloride. The methanol is added to the precipitate under room temperature for re-crystalization over night, and the crystal is filtered to obtain di-simvastatinic acid piperazinium salt complex (8.8 g).

Example 21

Preparation of Di-Rosuvastatinic Acid Piperazinium Salt (20)

The aqueous solution of sodium hydroxide (4 g/60 ml) is added into rosuvastatin (10.5 g) in ethanol (100 ml) under room temperature to result a solution of rosuvastatinic acid sodium in ethanol for use.

Piperazine di-hydrochloride (1.6 g) dissolved in the mixture of ethanol (100 ml) and water (30 ml) is added a solution of rosuvastatinic acid sodium dissolved in the hydrous ethanol for reacting at 50° C. for 60 mins. After cooling to room temperature, a white precipitate is obtained and filtered for removing the sodium hydrochloride. The methanol is added to the precipitate under room temperature for re-crystallization over night, and the crystal is filtered to obtain di-rosuvastatinic acid piperazinium salt complex (9.8 g)

Example 22

Preparation of Di-Atorvastatinic Acid Piperazinium Salt (21)

In a flask equipped with a magnetic stirrer, atorvastatin hemicalcium salt (13.6 g) suspended in a mixture of ethanol (100 ml) and water (30 ml) is poured. Piperazinium di-hydrochloride (1.6 g) dissolved in ethyl alcohol (150 ml) is added into the suspension under room temperature. The mixture is stirred continuously at 50° C. for 60 minutes until the reaction is completed. The mixture is filtered quickly and concentrated under reduced pressure. The mixture is then cooled to ambient temperature and water is added to the mixture. The mixture is stirred under room temperature for 20 minutes until the reaction is completed. After filtering the precipitate for removing calcium chloride, a white di-atorvastatinic acid piperazinium salt complex (20.2 g) is obtained.

Example 23

Preparation of KMUP-1-γ-Polyglutamate Complex (22)

(A) 2 g of sodium γ-polyglutamate is dissolved in water to form a 5% viscous aqueous solution (40 ml). 2 g of KMUP-1 HCl salt powder is added to the solution and the mixture is stirred at 50° C. for 1 hr to obtain a white precipitate. The solution is poured out and the ethanol (100 ml) is added for dehydration. Ethanol (100 ml) is added additionally to wash out the unreacted KMUP-1, and the precipitate is dry over night (50° C.) to obtain KMUP-1-γ-polyglutamate complex (2.6 g).

(B) 2 g of calcium γ-polyglutamate is dissolved in water to form a 5% viscous aqueous solution (40 ml). 2 g of KMUP-1 HCl salt powder is added to the solution and the mixture is stirred at 50° C. for 1 hr to obtain a white precipitate. The solution is poured out and the ethanol (100 ml) is added for dehydration. Ethanol (100 ml) is added additionally to wash out the unreacted KMUP-1, and the precipitate is dry over night (50° C.) to obtain KMUP-1-γ-polyglutamate complex (2.8 g).

(C) 2 g of γ-polyglutamate is dissolved in ethanol (50 ml), to which KMUP-1 powder (2 g) is added to the solution and the mixture is stirred at 50° C. for 1 hr and then incubated at room temperature to obtain a white precipitate. After the precipitate is filtered, the ethanol (100 ml) is added for washing out the unreacted KMUP-1, and the precipitate is dry over night (50° C.) to obtain KMUP-1-γ-polyglutamate complex (3.1 g).

Example 24

Preparation of KMUP-1-Polyglutamate-Alginate Sodium Complex (23)

Calcium polyglutamate-alginate sodium (2 g) is dissolved in water to form a 5% viscous aqueous solution (40 ml). KMUP-1 HCl salt powder (2 g) is added to the solution and the mixture is stirred at 50° C. for 1 hr to obtain a white precipitate. The solution is poured out and the ethanol (100 ml) is added for dehydration. Ethanol (100 ml) is added additionally to wash out the un-reacted KMUP-1, and the precipitate is dry over night (50° C.) to obtain KMUP-1-polyglutamate-alginate sodium complex (2.9 g).

Example 25

Preparation of KMUP-1-Carboxy Methyl Cellulose Complex 2 g of sodium carboxyl methyl cellulose is dissolved in water to form a 5% viscous aqueous gel solution (40 ml). 2 g of KMUP-1 HCl salt powder is added to the solution and the mixture is stirred at 50° C. for 1 hr to obtain a white precipitate. The solution, containing the white precipitate, is poured out and the ethanol (100 ml) is further added for dehydration and wash-out the unreacted KMUP-1 and resulted sodium chloride following filtration. The obtained precipitate is dried over night (50° C.) to have KMUP-1-Carboxy Methyl Cellulose complex (2.4 g).

Example 26

Preparation of KMUP-3 HCl Salt (24)

KMUP-3 (8.4 g) is dissolved in a mixture of ethanol (100 mL) and 1N HCl (60 mL) for reacting at 50° C. for 20 min After cooled to room temperature, a yellow precipitate is obtained and the methanol is added thereinto under room temperature and the solution is incubated over night for crystallization. The crystal is filtrated to obtain yellow KMUP-3 HCl salt (6.4 g).

Example 27

Preparation of KMUP-2 HCl Salt (25)

KMUP-2 (8.0 g) is dissolved in a mixture of ethanol (10 mL) and 1N HCl (60 mL) for reacting at 50° C. for 10 min. The methanol is added into the solution under room temperature and the solution is incubated over night for crystallization. The crystal is filtrated to obtain KMUP-2 HCl salt (6.4 g).

Example 29

Preparation of KMUP-1-PGI$_2$ Complex (27)

KMUP-1 HCl salt (0.9 mg) is dissolved in a mixture of ethanol (100 mL) and water (30 mL), to which PGI$_2$ sodium (1020 mg) dissolved in ethyl alcohol (300 mL) is added and the mixture for reacting at 50° C. for 20 mins. After cooling to the room temperature, a white precipitate is obtained, to which the methanol is added under room temperature and being incubated over night for re-crystallization. The crystal is filtered to obtain KMUP-1-PGI$_2$ complex (1.6 g).

Example 30

The Formulae of KMUP-1 And Rosuvastatin

|  |  |
| --- | --- |
| Rosuvastatin | 0.20 g |
| KMUP-1 HCl salt | 0.20 g |
| Lactose | qs |

REFERENCES

1. Evans M, Rees A. Effects of HMG-CoA reductase inhibitors on skeletal muscle: are all statins the same? Drug Safety 2002;25: 649-63.
2. Jacobson T A. Myopathy with statin-fibrate combination therapy: clinical considerations. Nat Rev Endocrinol. 2009 September; 5 (9):507-18.
3. Lipid Research Clinics Program. The lipid research clinics coronary primary prevention trial results. *JAMA* 1984;251: 351-74
4. Lin, R.-J., Wu, B.-N., Lo, Y.-C., Shen, K.-P., Lin, Y.-T., Huang, C.-H. and Chen, I.-J. KMUP-1 relaxes rabbit corpus cavernosum smooth muscle in vitro and in vivo: involvement of cyclic GMP and K$^+$ Channels. Br. J. Pharmacol. 2002. 135: 1159-1166.
5. Liu, C.-M., Lo, Y.-C., Wu, B.-N., Wu, W.-J., Chou, Y.-H., Huang C.-H., An, L.-M. and Chen, I.-J. cGMP-enhancing—an $\alpha_{1A}/\alpha_{1D}$-andrenoceptor blockade-derived inhibition of Rho-kinase by KMUP-1 provides optimal prostate relaxation and epithelial cell anti-proliferation efficiency. Prostate, 2007. 67: 1397-1410.
6. Wu, B.-N., Chen, C.-W., Liou, S.-F., Yeh, J.-L., Cluing, H.-H. & Chen, I.-J. Inhibition of proinflammatory tumor necrosis factor-α-Induced inducible nitric-oxide synthase by xanthine-based 7-[2-[4-(2-chlorobenzene)piperazinyl]ethyl]-1,3-dimethyl-xanthine (KMUP-1) and 7-[2-[4-(4-nitrobenzene)piperazinyl]-ethyl]-1,3-dimethylxanthine (KMUP-3) in rat trachea: The involvement of soluble guanylate cyclase and protein kinase G. Mol. Pharmacol. 2006. 70: 977-985.
7. Wu, B.-N., Lin, R.-J., Lin, C.-Y., Shen, K.-P., Chiang, L.-C. & Chen, I.-J. A xanthine-based KMUP-1 with cyclic GMP enhancing and K$^+$ channels opening activities in rat aortic smooth muscle. Br. J. Pharmacol. 2001. 134: 265-274.
8. Wu, B.-N., Lin, R.-J., Lo, Y.-C., Shen, K.-P., Wang, C.-C., Lin, Y.-T. and Chen, I.-J. KMUP-1, a xanthine derivative, induces relaxation of guinea-pig isolated trachea: the role of the epithelium, cyclic nucleotides and K$^+$ channels. Br. J. Pharmacol. 2004. 142: 1105-1114.
9. Wu, B.-N., Tu, H.-F., Welsh, D. G and Chen, I.-J. KMUP-1 activates BK$_{Ca}$ channels in basilar artery myocytes via cyclic nucleotide-dependent protein kinases. Br. J. Pharmacol. 2005. 146, 862-871.
10. Chung, H.-H., Dai, Z.-K, Wu B.-N, Yeh J.-L., Chai C.-Y., Chu, K.-S., Liu, C.-P., Chen, I.-J. (2010) The xanthine derivative KMUP-1 inhibits models of pulmonary artery hypertension via increased NO and cGMP-dependent inhibition of RhoA/Rho kinase. Br J Pharmacol 160 (4):971-86.

What is claimed is:

1. A complex compound represented by a structure being

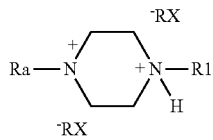

wherein R1 is one of a hydrogen and a benzene ring substituted with a substituting group being one selected from a group consisting of a halogen atom, an amino group, a nitro group, a C1~C5 alkyl group and a C1~C5 alkoxy group;

Ra is one of a hydrogen and a xanthine group substituted with a substituting group being one selected from a group consisting of a halogen atom, an amino group, a nitro group, a C1~C5 alkyl group and a C1~C5 alkoxy group; and RX contains a carboxylic group donated from one selected from a group consisting of an organic acid, a statin, a fibric acid, a fibric acid derivative, a non-steroid anti-inflammatory (NSAIDs), an anti-allergy drug, an anti-diabetic drug and an anti-asthmatic drug, wherein RX$^{31}$ is an anion form of the carboxylic group.

2. A compound as claimed in claim 1, wherein the halogen atom is one of a chlorine atom and a fluorine atom.

3. A compound as claimed in claim 1, wherein RX is an organic acid being one selected from a group consisting of a citric acid, a fumaric acid, a maleic acid, a nicotinic acid, an isonicotinic acid, a tartaric acid, a succinic acid, an adipic acid, a fatty acid, a methanesulfonic acid and a phenoxylevulinic acid.

4. A compound as claimed in claim 1, wherein RX is a statin being one selected from a group consisting of atorvastatin, cerivastatin, fluvastatin, lovastatin, mevastatin, pravastatin, rosuvastatin, pitavastatin and simvastatin.

5. A compound as claimed in claim 1, wherein RX is an NSAID being one selected from a group consisting of Aspirin, Salicylic acid, indomethacin, diclofenac, meclofenamic acid, tolmetin, ketoprofen, methotrexate, flurbiprofen, fenoprofen, tiaprofen, diflunisal, etodolac, ibuprofen and prostacyclin.

6. A compound as claimed in claim 1, wherein RX is an anti-asthmatic drug being one selected from a group consisting of a montelukast, a cromolyn sodium and a nedocromil.

7. A compound as claimed in claim 1, wherein RX is a fibric acid derivative being one of a gemfibrozil and a fenofibrate.

8. A compound as claimed in claim 1, wherein RX is an anti-diabetic drug being one selected from a group consisting of an alginate sodium, a γ-polyglutamic acid, a sodium polyglutamate, a calcium polyglutamate-alginate sodium, a repaglinide and a nateglinide.

9. A pharmaceutical composition, comprising :
- an effective amount of one of a KMUP salt and a piperazinium salt;
- an effective amount of a first compound containing a carboxylic group donated from one selected from a group consisting of a statin, a non-steroid anti-inflammatory (NSAIDs), an anti-allergy drug, an anti-diabetic drug and an anti-asthmatic drug; and
- an effective amount of a second compound containing a carboxylic group donated from one selected from a group consisting of a statin, a non-steroid anti-inflammatory (NSAIDs), an anti-allergy drug, an anti-diabetic drug and an anti-asthmatic drug.

10. A pharmaceutical composition as claimed in claim 9, wherein the KMUP salt is one of a mineral acid salt and an organic acid salt.

11. A pharmaceutical composition as claimed in claim 9, wherein the piperazinium salt is one of a mineral acid salt and an organic acid salt.

12. A pharmaceutical composition as claimed in claim 9, further comprising a pharmaceutically accepted carrier.

* * * * *